US011337391B2

(12) United States Patent
Marks et al.

(10) Patent No.: US 11,337,391 B2
(45) Date of Patent: May 24, 2022

(54) EARLY FLOWERING PLANTS

(71) Applicant: Regents of the University of Minnesota, Minneapolis, MN (US)

(72) Inventors: Michael David Marks, Roseville, MN (US); Kevin Dorn, Roseville, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 16/104,318

(22) Filed: Aug. 17, 2018

(65) Prior Publication Data

US 2019/0053457 A1 Feb. 21, 2019

Related U.S. Application Data

(60) Provisional application No. 62/547,668, filed on Aug. 18, 2017.

(51) Int. Cl.
*A01H 6/20* (2018.01)
*A01H 5/02* (2018.01)
*C12N 9/02* (2006.01)
*C07K 14/415* (2006.01)
*A01H 5/10* (2018.01)

(52) U.S. Cl.
CPC ............ *A01H 6/20* (2018.05); *A01H 5/02* (2013.01); *A01H 5/10* (2013.01); *C07K 14/415* (2013.01); *C12N 9/0071* (2013.01)

(58) Field of Classification Search
None
See application file for complete search history.

(56) References Cited

U.S. PATENT DOCUMENTS

| | | |
|---|---|---|
| 2008/0160530 A1 | 7/2008 | Li |
| 2015/0143573 A1 | 5/2015 | Denolf et al. |
| 2017/0051299 A1 | 2/2017 | Fabijanski et al. |
| 2019/0053458 A1 | 2/2019 | Marks et al. |
| 2020/0131523 A1 | 4/2020 | Marks et al. |
| 2020/0308596 A1 | 10/2020 | Marks et al. |
| 2020/0370062 A1 | 11/2020 | Marks et al. |

FOREIGN PATENT DOCUMENTS

| | | |
|---|---|---|
| WO | WO 2000/036114 | 6/2000 |
| WO | WO 2006/052912 | 5/2006 |
| WO | WO 2013/112578 | 8/2013 |
| WO | WO 2017/004375 | 1/2017 |
| WO | WO 2017/117633 | 7/2017 |
| WO | WO 2018/140782 | 8/2018 |

OTHER PUBLICATIONS

Kano-Murakami et al (1993, "A Rice Homeotic Gene, OSH1, Causes Unusual Phenotypes in Transgenic Tobacco", FEBS 334:365-368).*

Yu et al (2008, "Modulation of Brassinosteroid-Regulated Gene Expression by Jumonji Domain-Containing Proteins ELF6 and REF6", PNAS105(21): 7618-7623).*
Yu et al. (2008), "Modulation of Brassinosteroid-Regulated Gene Expression by Jumonji Domain-Containing Proteins ELF6 and REF6", PNAS105(21): pp. 7618-7623. (Year: 2008).*
Baud et al., "Physiological and developmental regulation of seed oil production," Prog Lipid Res., 49(3):235-49, Jul. 2010.
Belide et al., "Modification of seed oil composition in *Arabidopsis* by artificial microRNA-mediated gene silencing," Frontiers in plant science, 3:168, Jul. 2012.
Bell, "Factors affecting the nutritional value of canola meal: a review," Canadian Journal of Animal Science, 73(4):679-697, Dec. 1993.
Bligh et al., "A rapid method of total lipid extraction and purification," Canadian Journal of Biochemistry and Physiology, 37(8):911-917, Aug. 1959.
Boateng et al., "Producing stable pyrolysis liquids from the oil-seed presscakes of mustard family plants: Pennycress (*Thlaspi arvense* L.) and Camelina (*Camelina sativa*)," Energy & Fuels, 24(12):6624-6632, Nov. 2010.
Calver et al., "Identification of target genes and processes involved in erucic acid accumulation during seed development in the biodiesel feedstock Pennycress (*Thlaspi arvense* L.)," J. Plant Physiol., 208:7-16, Jan. 2017.
Chopra et al., "The adaptable use of *Brassica* NIRS calibration equations to identify pennycress variants to facilitate the rapid domestication of a new winter oilseed crop," Industrial Crops and Products, 128:55-61, Feb. 2019.
Chopra et al., "Transcriptome profiling and validation of gene based single nucleotide polymorphisms (SNPs) in sorghum genotypes with contrasting responses to cold stress," BMC Genomics, 16(1):1040, Dec. 2015.
Chopra et al., "Translational genomics using *Arabidopsis* as a model enables the characterization of pennycress genes through forward and reverse genetics," The Plant Journal, 96(6):1093-1105, Dec. 2018.
Crevillén et al., "Epigenetic reprogramming that prevents transgenerational inheritance of the vernalized state," Nature, 515(7528):587-90, Nov. 2014.
Dorn et al., "D e novo assembly of the pennycress (*Thlaspi arvense*) transcriptome provides tools for the development of a winter cover crop and biodiesel feedstock," The Plant Journal, 75(6):1028-38, Sep. 2013.
Fauser et al., "Both CRISPR/C as-based nucleases and nickases can be used efficiently for genome engineering in *Arabidopsis thaliana*," Plant J., 79(2):348-359, Jul. 2014.

(Continued)

Primary Examiner — Russell Kallis
(74) Attorney, Agent, or Firm — Fish & Richardson P.C.

(57) ABSTRACT

This document relates to materials and methods for generating early flowering oilseed (e.g., pennycress) plants. For example, oilseed plants (e.g., modified oilseed plants) having one or more modifications in a polypeptide involved in early flowering (e.g., early flowering six (ELF6)), as well as materials and methods for making and using early flowering oilseed plants are provided.

6 Claims, 11 Drawing Sheets

Specification includes a Sequence Listing.

(56) References Cited

OTHER PUBLICATIONS

Ferrándiz et al., "Negative regulation of the SHATTERPROOF genes by FRUITFULL during *Arabidopsis* fruit development," Science, 289(5478):436-438, Jul. 2000.
Girin et al., "Brassicaceae INDEHISCENT genes specify valve margin cell fate and repress replum formation," Plant J., 63(2):329-338, Jul. 2010.
Golebiowski et al., "Near infrared reflectance spectroscopy of oil in intact canola seed (*Brassica napus* L.). II. Association between principal components and oil content," Journal of near Infrared Spectroscopy, 13(5):255-264, Oct. 2005.
Han et al., "Functional characterization of beta-ketoacyl-CoA synthase genes from *Brassica napus* L," Plant molecular biology, 46(2):229-39, May 2001.
Kim et al., "Toward production of jet fuel functionality in oilseeds: identification of FatB acyl-acyl carrier protein thioesterases and evaluation of combinatorial expression strategies in Camelina seeds," Journal of Experimental Botany, 66(14):4251-4265, May 2015.
Liljegren et al., "SHATTERPROOF MADS-box genes control seed dispersal in *Arabidopsis*," Nature, 404(6779):766-770, Apr. 2000.
McGinn et al., "Molecular tools enabling pennycress (*Thlaspi arvense*) as a modelplant and oilseed cash cover crop," Plant Biotechnology Journal, 17(4):776-788, Apr. 2019.
Montero de Espinosa et al., "Plant oils: the perfect renewable resource for polymer science?!" European Polymer Journal, 47(5):837-852, May 2011.
Moser et al., "Composition and physical properties of cress (*Lepidium sativum* L.) and field pennycress (*Thlaspi arvense* L.) oils," Industrial Crops and Products, 30(2):199-205, Sep. 2009.
Moser et al., "Production and evaluation of biodiesel from field pennycress (*Thlaspi arvense* L.) oil," Energy & Fuels, 23(8):4149-4155, Jul. 2009.
Phippen et al., "Soybean seed yield and quality as a response to field pennycress residue," Crop Science, 52(6):2767-2773, Nov. 2012.
Riu et al., "[Detection of erucic acid and glucosinolate in intact rapeseed by near-infrared diffuse reflectance spectroscopy]," Spectroscopy and Spectral Analysis, Dec. 2006, 26(12):2190-2192, (with English abstract).
Roeder et al., "The role of the REPLUMLESS homeodomain protein in patterning the *Arabidopsis* fruit," Curr. Biol., 13(18):1630-1635, Sep. 2003.
Rosas et al., "One-step, codominant detection of imidazolinone resistance mutations in weedy rice (*Oryza sativa* L.)," Electron. J. Biotechnol., 17:95-101, Mar. 2014.
Roscoe et al., "Mutations in the fatty acid elongation 1 gene are associated with a loss of β-ketoacyl-CoA synthase activity in low erucic acid rapeseed," FEBS letters, 492(1-2):107-11, Mar. 2001.
Sedbrook et al., "New approaches to facilitate rapid domestication of a wild plant to an oilseed crop: example pennycress (*Thlaspi arvense* L.)," Plant Sci., 227:122-32, Oct. 2014.
Sedbrook et al., "New approaches to facilitate rapid domestication of a wild plant to an oilseed crop: example pennycress (*Thlaspi arvense* L.)," Plant Science, 227:122-132, Oct. 2014.
Sidhu et al., "Diode Array Near Infrared Spectrometer Calibrations for Composition Analysis of Single Plant Canola (*Brassica napus*) Seed," Applied Engineering in Agriculture, 30(1):69-76, Jan. 2014.
Steinert et al., "Highly efficient heritable plant genome engineering using Cas9 orthologues from *Streptococcus thermophilus* and *Staphylococcus aureus*," Plant J., 84:1295-305, Dec. 2015.
Warwick et al., "The biology of Canadian weeds. 9. *Thlaspi arvense* L.(updated)," Canadian Journal of Plant Science, 82(4):803-823, Oct. 2002.
Wu et al., "Zero erucic acid trait of rapeseed (*Brassica napus* L.) results from a deletion of four base pairs in the fatty acid elongase 1 gene," Theoretical and applied genetics, 116(4):491-9, Feb. 2008.
Xin et al., "Mid-infrared spectral characteristics of lipid molecular structures in Brassica carinata seeds: relationship to oil content, fatty acid and glucosinolate profiles, polyphenols, and condensed tannins," J. Agric. Food Chem., 62(32):7977-7988, Aug. 2014.

Britt, "From stinkweed to oilseed," Nat. Food, 1:24-25, Jan. 2020.
Chopra et al., "Identification and stacking of crucial traits required for the domestication of pennycress," Nat. Food, 1:84-91, Jan. 2020.
Claver et al., "Identification of target genes and processes involved in erucic acid accumulation during seed development in the biodiesel feedstock Pennycress (*Thlaspi arvense* L.)," Journal of plant physiology, 208:7-16, Jan. 2017.
Downey and Craig, "Genetic control of fatty acid biosynthesis in rapeseed (*Brassica napus* L.)," Journal of the American Oil Chemists' Society, Jul;41(7):475-8, Jul. 1964.
Fourmann et al., "The two genes homologous to *Arabidopsis* FAE1 co-segregate with the two loci governing erucic acid content in *Brassica napus*," Theor. Appl. Genet., 96(6-7):852-8, May 1998.
James et al., "Directed Tagging of the *Arabidopsis* Fatty Acid Elongation! (FAE1) Gene with the Maize Transposon Activator," The Plant Cell, 7:309-319, Mar. 1995.
Javidfar and Cheng, "Single locus, multiallelic inheritance of erucic acid content and linkage mapping of FAE1 gene in yellow mustard," Crop Science, 53(3):825-32, May 2013.
Bai et al., "The Biochemistry of Headgroup Exchange During Triacylglycerol Synthesis in Canola," The Plant Journal, 103(1):83-94, Jan. 2020.
GenBank Accession No. KT223025.1, "Thlaspi arvense cultivar French 3-keloacyl-CoA synthase (FAE1) mRNA, complete cds," Nov. 29, 2015, 2 pages.
Katavic et al., "Alteration of Seed Fatty Acid Composition by an Ethyl Methanesulfonate-induced Mutation in *Arabidopsis thaliana* Affecting Diacylglycerol Acyltransferase Activity," Plant Physiology, May 1995, 108(1):399-409.
Lu et al., "*Arabidopsis* Mutants Deficient in Diacylglycerol Acyltransferase Display Increased Sensitivity to Abscisic Acid, Sugars, and Osmotic Stress During Gemination and Seedling Development," Plant Physiology, Jul. 2002, 129(3):1352-1358.
Lu et al., "Expression pattern of diacylglycerol acyltransferase-1, an enzyme involved in triacylglycerol biosynthesis, in *Arabidopsis thaliana*," Plant Mol. Biology, May 2003, 52(1):31-41.
Routaboul et al., "The TAG1 locus of *Arabidopsis* encodes for a diacylglycerol acyltransferase," Plant Physiol Biochemistry, Nov. 1999, 37(10:831-840.
Sanyal et al., "Stearic sunflower oil as a sustainable and healthy alternative to palm oil. A review" Agron. Sustain. Development, May 17, 2017, 37:18, 11 pages.
van Gelderen et al, "An INDEHISCENT-Controlled Auxin Response Specifies the Separation Layer in Early *Arabidopsis* Fruit," Molecular Plant, Jun. 2016, 9:857-869.
Vogel et al., "Expression of the Arabidopsis WRINKLED 1 transcription factor leads to higher accumulation of palraitate in soybean seed," Plant Biotechnol. Journal. Jan. 17, 2019, 17(7):1369-1379.
Xie et al., "RNA-Guided Genome Editing in Plants Using a CRISPR-Cas System," Molecular Plant, Nov. 2013, 6(6):1975-1983.
Zarhloul et al., "Breeding high-steric oilseed rape (*Brassica napus*) with high- and low-erucic background using optimised promoter-gene constructs." Mol. Breeding. Sep. 2006, 18(3):241-251.
Zou et al., "The *Arabidopsis thaliana* TAG1 mutant has a mutation in a diacylglycerol acyltransferase gene.," The Plant Journal, Sep. 1999, 19(6):645-653.
U.S. Appl. No. 16/969,434, filed Aug. 12, 2020, Michael David Marks, Published.
U.S. Appl. No. 16/831,145, filed Mar. 26, 2020, Michael David Marks, Published.
Blacklock et al., "Substrate specificity of *Arabidopsis* 3-ketoacyl-CoA synthases," Biochem. Biophys. Res. Communications, Jun. 5, 2006, 346(2):583-590.
Joubes et al., "The VLCFA elongase gene family in *Arabidopsis thaliana*: phylogenetic analysis, 3D modelling and expression profiling," Plant Mol. Biology, May 9, 2008, 67(5).547-566.
Millar et al., "Very-long-chain fatty acid biosynthesis is controlled through the expression and specificity of the condensing enzyme," Plant Journal, Jul. 1997, 12(1):121-131.
Morineau et al., "Dual Fatty Acid Elongase Complex Interactions in *Arabidopsis*," PLoS One. Sep. 1, 2016, 11(9):e0160631, 20 pages.

(56) References Cited

OTHER PUBLICATIONS

Wang et al., "A functional genomics resource for *Brassica napus*: development of an EMS mutagenized population and discovery of FAE1 point mutations by TILLING," New Phytologist, Dec. 2008, 180(4):751-765.

Claver et al., "Functional analysis of β-ketoacyl-CoA synthase from biofuel feedstock Thlaspi arvense reveals differences in the triacylglycerol biosynthetic pathway among Brassicaceae," Plant Mol. Biology, 104(3):283-296, Aug. 1, 2020.

GenBank Accession No. AAC49186.1, "beta-ketoacyl-CoA synthase [*Simmondsia chinensis*]," dated Oct. 31, 1995, 2 pages.

GenBank Accession No. NP_195178.1, "3-ketoacyl-CoA synthase 18 [*Arabidopsis thaliana*]." dated Jan. 22, 2014, 2 pages.

Gigolashvili et al., "The R2R3-MYB transcription factor HAG1/MYB28 is a regulator of methionine-derived glucosinolate biosynthesis in *Arabidopsis thaliana*," Plant Journal, 51(2):247-261, Jul. 2007.

Haslam et al., "Extending the story of very-long-chain fatty acid elongation," Plant Science, 210:93-107, Sep. 2013.

Kafri et al., "The regulatory utilization of genetic redundancy through responsive backup circuits," Proc. Nat. Acad. Sci. USA~, 103(31):1653-11658, Aug. 2006.

Lassner et at, "A jojoba beta-Ketoacyl-CoA synthase cDNA complements the canola fatty acid elongation mutation in transgenic plants," Plant Cell, 8(2):281-292, Feb. 1996.

Shen et al., "Resistance gene candidates identified by PCR with degenerate oligonucleotide primers map to clusters of resistance genes in lettuce," Mol. Plant Microbe Interactions, 11(8):815-823, Aug. 1998.

Blande et al. (GenBank Sequence Accession No. GEVK01020461.1, Published Nov. 4, 2016).

Batsale et al., "Biosynthesis and Functions of Very-Long-Chain Fatty Acids in the Responses of Plants to Abiotic and Biotic Stresses," Cells, May 21, 2021, 10:1284, 26 pages.

Dorn et al., "A draft genome of field pennycress (Thlaspi arvense) provides tools for the domestication of a new winter biofuel crop," DNA Research, Apr. 2015, 22(2):121-131.

ENA Accession No. PRJEB46635, "Chromosome-level Thlaspi arvense genome provides new tools for translational research and for a newly domesticated cash cover crop of the cooler climates," dated Aug. 2, 2021, 2 pages.

GenBank Accession No. AZNP01000000.1, "Thlaspi arvense cultivar MN106, whole genome shotgun sequencing project," dated Mar. 19, 2015, 1 page.

Geng et al., "Genomic analysis of field pennycress (Thlaspi arvense) provides insights into mechanisms of adaptation to high elevation," BMC Biology, Jul. 22, 2021, 19:143, 14 pages.

Nunn et al., "Chromosome-level Thlaspi arvense genome provides new tools for translational research and for a newly domesticated cash cover crop of the cooler climates," bioRxiv, Aug. 1, 2021, 48 pages.

Tresch et al., "Inhibition of saturated very-long-chain fatty acid biosynthesis by mefluidide and perfluidone: selective inhibitors of 3-ketoacyl-CoA synthases," Phytochemistry, Apr. 2012, 76:162-171.

Yang et al.. "Comprehensive analysis of KCS gene family in Citrinae reveals the involvement of CsKCS2 and CsKCS11 in fruit cuticular wax svnthesis at ripening," Plant Science, Sep. 2021, 310:110972, 11 pages.

Zeng et al. (Plant cell, 26:2648-2659, Jun. 2014).

* cited by examiner

CGTCCAAGCAGAAGAACATGG→ATATTGTTGATGAAATGGAAGGTACTGCAGGCTGGAAGCTC
TCCAACAGTTCATGGAACCTTCAGATGATTGCACGTTCACCTGGATCTGTTACACGCTTCATGCC
AGATGACATCCCTGGTGTCACATCTCCCATGGTTTATATCGGTATGTTGTTCAGCTGGTTTGCCT
GGCACGTTGAGGACCATGAGCTTCACAGTATGAATTACCTTCACACTGGCTCGCCAAAGACGTGG
TACGCTGTCCCTGGTGATTATGCATTTGACTTTGAAGAGGTTATCCGCAAAAATTCGTATG←GC
AGAAACATTGATCAACTGG

C = C>T mutation in A7-25 mutant
REVERSE primer
FORWARD primer

FIG. 4A

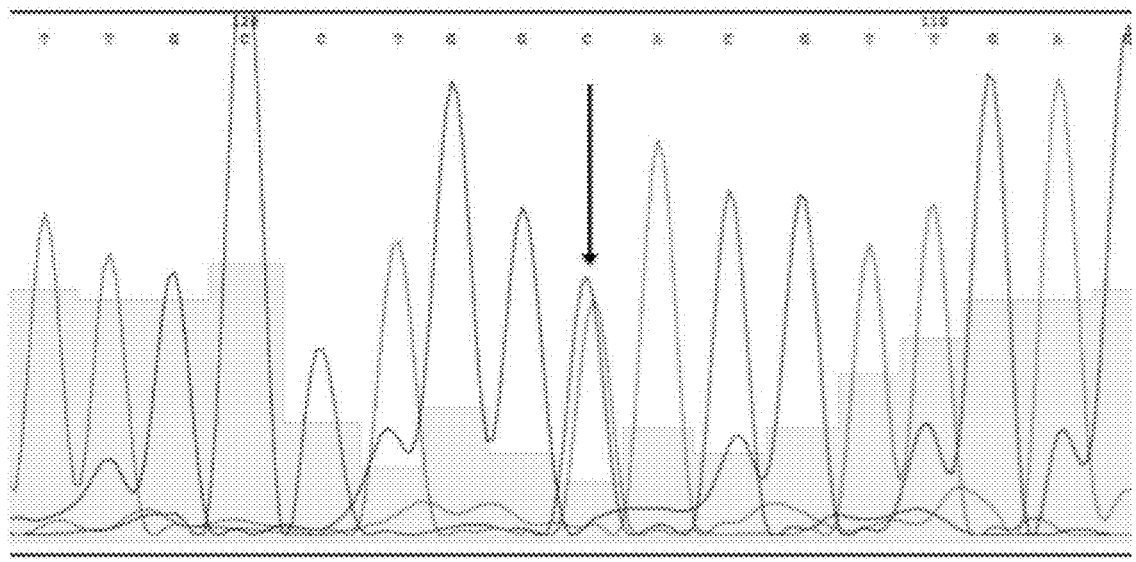

FIG. 4B

```
At_ELF6         --------------MGNVEIPNWLKALPLAPVFRPTDTEFADPIAYISKIEKEASAFGIC
Ta_ELF6         --------------MGDVEIPNWLKALPLAPVFRPTDTEFADPIAYISKIEKEASAFGIC
Ta_ELF6_mutant  --------------MGDVEIPNWLKALPLAPVFRPTDTEFADPIAYISKIEKEASAFGIC
                               :* **:.** ** .***::*******::*:;*:**; ;***

At_ELF6         KIIPPLPKPSKKYVFYNLNKSLLKCPELVSDVDISKVCKE--------------DRAVFTT
Ta_ELF6         KIIPPLPKPSKKYVFYNLNKSLLRCPELASDVDISKVCQE--------------DRAVFTT
Ta_ELF6_mutant  KIIPPLPKPSKKYVFYNLNKSLLRCPELASDVDISKVCQE--------------DRAVFTT
                *:*** *:**:::*: :**.**   . :                          ****

At_ELF6         RQQELGQTVKKNK-GEKGKSNSQRSGVKQVWQSGGVYTLDQFEAKSKAFYKTQLGTVKEL
Ta_ELF6         RQQELGQAVKRKKGGESSKSNSQRSGVKQVWQSGGVYTLEQFESKSKTFYKSQLGTTKEV
Ta_ELF6_mutant  RQQELGQAVKRKKGGESSKSNSQRSGVKQVWQSGGVYTLEQFESKSKTFYKSQLGTTKEV
                *:****:        .       *******  ***:***:**: * :: :. ::

At_ELF6         APVVIEALFWKAALEKPIYIEYANDVPGSAFGEPEDHFRHFRQRKRRGRGFYQRKTENN-
Ta_ELF6         PPVVVEALFWKAALEKPIYIEYANDVPGSAFGEPEGHFRHFRQRKRRGRGFYQRKAEVSE
Ta_ELF6_mutant  PPVVVEALFWKAALEKPIYIEYANDVPGSAFGEPEGHFRHFRQRKRRGRGFYQRKAEVSE
                 .:*::***::  ::****:*********.*             ::

At_ELF6         -----------DPSG-------KNGEKSSPEVEKAPLAST---SLSSQDSSKQKNMDIVD
Ta_ELF6         DSGVENGTNSQEPTC-------KNGEKTLPEVAKASLASP---SLLSQDPSKQKNMDIVD
Ta_ELF6_mutant  DSGVENGTNSQEPTC-------KNGEKTLPEVAKASLASP---SLLSQDPSKQKNMDIVD
                                                                           :

At_ELF6         EMEGTAGWKLSNSSWNLQMIARSPGSVTRFMPDDIPGVTSPMVYIGMLFSWFAWHVEDHE
Ta_ELF6         EMEGTAGWKLSNSSWNLQMIARSPGSVTRFMPDDIPGVTSPMVYIGMLFSWFAWHVEDHE
Ta_ELF6_mutant  EMEGTAGWKLSNSSWNLQMIARSPGSVTRFMPDDIPGVTSPMVYIGMLFSWFAWYVEDHE
                *  :  ::**;:** **** ***; **:******:*****************;****;

At_ELF6         LHSMNYLHTGSPKTWYAVPCDYALDFEEVIRKNSYGRNIDQLAALTQLGEKTTLVSPEMI
Ta_ELF6         LHSMNYLHTGSPKTWYAVPGDYAFDFEEVIRKNSYGRNIDQLAALTQLGEKTTLVSPEMI
Ta_ELF6_mutant  LHSMNYLHTGSPKTWYAVPGDYAFDFEEVIRKNSYGRNIDQLAALTQLGEKTTLVSPEMI
                ***:*:****: ******* * *: :*****  .*. . * ::*:* *******:***::

At_ELF6         VASGIPCCRLVQNPGEFVVTFPRSYHVGFSHGFNCGEAANFGTPQWLNVAKEAAVRRAAM
Ta_ELF6         IASDIPCCRLVQNPGEFVVTFPRSYHVGFSHGFNCGEAANFGTPQWLNVAKEAAVRRAAM
Ta_ELF6_mutant  IASDIPCCRLVQNPGEFVVTFPRSYHVGFSHGFNCGEAANFGTPQWLNVAKEAAVRRAAM
                :..:;*****.* ********;********************.*****  *********.*

At_ELF6         NYLPMLSHQQLLYLLTMSFVSR-------VPRSLLPGGRSSRLRDRQREEREFLVKRAFV
Ta_ELF6         NYLPMLSHQQLLYLLTMSFVSRQISMASLVPRSLLPGGRSSRLRDRQREEREFLVKKAFV
Ta_ELF6_mutant  NYLPMLSHQQLLYLLTMSFVSRQISMASLVPRSLLPGGRSSRLRDRQREEREFLVKKAFV
                **************::**;*          ** ** * *;******;*:**;***; *;

At_ELF6         EDILNENKNLSVLLREP-GSRLVMWDPDLLPRHSALALAAAGVGAGA--SAVSPPAVAKKE
Ta_ELF6         EDILNENKNLSVLHREP-GFRLVMWDPDLLPRHSVHGLVTVG---G--AAVSSPAEGKNE
Ta_ELF6_mutant  EDILNENKNLSVLHREP-GFRLVMWDPDLLPRHSVHGLVTVG---G--AAVSSPAEGKNE
                :*:  .*:.  :    :     ;:*: *:**

At_ELF6         LEEGHSE-LQNKEKTSLLEELSL------FMEKLNDVYYDDDDGLLNDFQVDTGTLPCVAC
Ta_ELF6         LE------EKNKEKTTLLEELSL------FMEKLKDVYYDDDDGLLNDFQVDSGTLACVAC
Ta_ELF6_mutant  LE------EKNKEKTTLLEELSL------FMEKLKDVYYDDDDGLLNDFQVDSGTLACVAC
                          :. .*      :  ..     ;   .:. *:*:*  *;  *
```

FIG. 4C

```
At_ELF6          GVLGPPFMSVVQPSEKALKDLSERQGETD--A-------QEIM----------------
Ta_ELF6          GVLGPPFMSVVQPSENALNDLSERRGEID--G-------QEIT----------------
Ta_ELF6_mutant   GVLGPPFMSVVQPSENALNDLSERRGEID--G-------QEIT----------------
                 *:**:***::.:**:.:    .:

At_ELF6          ------------------------------------------------------------
Ta_ELF6          ------------------------------------------------------------
Ta_ELF6_mutant   ------------------------------------------------------------

At_ELF6          -------------------------------TLSSEKSDCEWKTSSRYIRPRIFCLEHTIELQR
Ta_ELF6          -------------------------------ALLSEKSDCEWNMSSRYIRPRIFCLEHTIELQR
Ta_ELF6_mutant   -------------------------------ALLSEKSDCEWNMSSRYIRPRIPCLEHTIELQR
                                                  **:****:*:::  .

At_ELF6          LLQSRGGLKFLVICHKDFQKFKAHAAIVAEEVKVPFSYDDVLLESASQEELSLIDLAIED
Ta_ELF6          LLESRGGLKFLVICHKDFQKFKAYAAIVAEEVKVPFSYDDILLESASKEELSLIDLAIED
Ta_ELF6_mutant   LLESRGGLKFLVICHKDFQKFKAYAAIVAEEVKVPFSYDDILLESASKEELSLIDLAIED
                 :*  *:** ; *:*** *: *:::  *  ;***;    *.*.:: * ,** .* **:::*

At_ELF6          EEKYEHSVDWTSELGINLRYCVKVRKNSPTKKIQHALSLGGLFSDTSQMLD--FTTIRWLQ
Ta_ELF6          EENNEHGVDWTSKLGINLRYCVKVRKNSPSTKIQHALSLGGLFSDTNHMLD-MSTIKWLQ
Ta_ELF6_mutant   EENNEHGVDWTSKLGINLRYCVKVRKNSPSTKIQHALSLGGLFSDTNHMLD-MSTIKWLQ
                 *   ;   ***  ..:**; . : :.: * .:         : *:.       :.*

At_ELF6          RKSRSKAKPSSTSSFTPCEHLEVKADGKLR--DNLDSQTGKKEEKIIQYSRKKKLNPKPS
Ta_ELF6          RKSRSKAKPSCTSSFTPREHLEVKVDRKLGEKEKVESQAGRKEEKIIQYSRKKKLKPKPS
Ta_ELF6_mutant   RKSRSKAKPSCTSSFTPREHLEVKVDRKLGEKEKVESQAGRKEEKIIQYSRKKKLKPKPS
                 *: *:      ::    :.               .          :  ..:   .

At_ELF6          AEQVQELA-TLAKSKDFDKTCK-----NFSSRSHLDSAIRSEMNSE-IGDSGRVIG----
Ta_ELF6          EERSQELT-ISAKSEDFENTCN-----TLAKRSHHGAMHSDMNNE-IGDPGR-NG----
Ta_ELF6_mutant   EERSQELT-ISAKSEDFENTCN-----TLAKRSHHGAMHSDMNNE-IGDFGR-NG----
                         .:                                             .   .

At_ELF6          VSFSINPCS-SSFTVGHGQ--------------------------------
Ta_ELF6          VSFSENHCS-SPFTGARGQ--------------------------------
Ta_ELF6_mutant   VSFSENHCS-SPFTGARGQ--------------------------------
                      :  .

At_ELF6          ----EHPEITVKFGSDLDGNVTNSLSM--------VNGDSADLTLTSISRE--------
Ta_ELF6          ---EHPKIIIKFGSALHGNITSSSSL--------VNGISADLTSV---TR---------
Ta_ELF6_mutant   ---EHPKIIIKFGSALHGNITSSSSL--------VNGISADLTSV---TR---------
                        :   .           :  ....  .

At_ELF6          -----------------------QHQGHSMT-SNNNGS--NSGSHVVASQTILVSTG
Ta_ELF6          -----------------------EHQGHSMT-SNNNGS--NS--------------
Ta_ELF6_mutant   -----------------------EHQGHSMT-SNNNGS--NS--------------
                                            ..
```

FIG. 4C (continued)

```
At_ELF6           DNHDGPRKLSGDYVCSDVSVRGIQEAVEMSDQEPGEPRSTVTNIEDEQQS--QIVKPTQR
Ta_ELF6           SNHDGPIKLSGEHV-SDVSVRDVDEAVEMSDQEFEELRSTVTNIEEEQQS--EMVRPTAL
Ta_ELF6_mutant    SNHDGPIKLSGEHV-SDVSVRDVDEAVEMSDQEFEELRSTVTNIEEEQQS--EMVRPTAL
                   : :                  :.              : :   .

At_ELF6           E---------------AVFGDHEQVEGAEAVSTREN-LCSEIILHTEHS---SAHVGMEIP
Ta_ELF6           ---------------------QVEGEESMCTREI-LSSEDIMHTEQQQEQTQLGLEVP
Ta_ELF6_mutant    ---------------------QVEGEESMCTREI-LSSEDIMHTEQQQEQTQLGLEVP
                                         :

At_ELF6           DINTASENLVVDM----------------THD---------GEPLES---SD------
Ta_ELF6           ETDIASENIVVDM----------------IHD---------DEPLAT---RD------
Ta_ELF6_mutant    ETDIASENIVVDM----------------IHD---------DEPLAT---RD------
                   :: :                                                    *

At_ELF6           ---ILSS------SNGDEASSNGLQVLNDELSMESEVSS---------------SENTEV
Ta_ELF6           ---ILSS------SNGDQASSNGLQALDNELSMESEVAS---------------SENTEV
Ta_ELF6_mutant    ---ILSS------SNGDQASSNGLQALDNELSMESEVAS---------------SENTEV
                     ::         .. : :              . .                 : .

At_ELF6           IEAP---NSMGEAKKKR-KIESESETNDNPESSIGFIRSPCEGLRSRGKRKATCETSLKHT
Ta_ELF6           IEASPNSIMREANKKR-RIESESETNDNPDGSIGFIRSPCEGLRSRGRRRVTREASVSLT
Ta_ELF6_mutant    IEASPNSIMREANKKR-RIESESETNDNPDGSIGFIRSPCEGLRSRGRRRVTREASVSLT
                   ::              .    .    .*;*****.** *              .

At_ELF6           ETSDEEKKPIAKRLKKTPKACSGSRQQEVPTTTHPNRCYLEGCKMTFESKAKLQTHKRNR
Ta_ELF6           ETSDEEKKPAAKRPKKTPKTRSGSHHQEDSTTSHHNRCNLEGCKMTFKSKAELQAHQRNR
Ta_ELF6_mutant    ETSDEEKKPAAKRPKKTPKTRSGSHHQEDSTTSHHNRCNLEGCKMTFKSKAELQAHQRNR
                                    :     :*   ::  * *:*:*.:*   *::*

At_ELF6           CTHEGCGKKFRAHKYLVLHQRVHKDERPFECSWKGCSMTFKWQWARTEHLRLHTGERPYI
Ta_ELF6           CAHEGCGKKFRAHKYLVLHQRVHNDDRPFVCSWKGCSMTFKWPWARTEHLRLHTGERPYK
Ta_ELF6_mutant    CAHEGCGKKFRAHKYLVLHQRVHNDDRPFVCSWKGCSMTFKWPWARTEHLRLHTGERPYK
                  * *.* *;* ;***    ** **  ;:**; * *.** *;*** **;***;*;****;**

At_ELF6           CKVDGCGLSFRFVSDYSRHRRKTMHYVT---
Ta_ELF6           CKVDGCGMSFRFVSDYSRHRRKKGHYVT---
Ta_ELF6_mutant    CKVDGCGMSFRFVSDYSRHRRKKGHYVT---
                  *.. .** ;**;**.;****;*  *;
```

FIG. 4C (continued)

```
Os_ROD1         ---MPPPPPPSLTANTASSMGNAEAVVVLPANGGARRRADKVVHPAPMPDRAAGGAMERE
Sl_ROD1         ---MNAET-LHLRYSSSSSFNT---RSHSSINGFQF---------ENMEMEDDNK-ITDM
Gm_ROD1         ------------------------------MNGGAEASLNHRRKHQTAPADGAKG-VKVA
At_ROD1         MSAAAAETDVSLRRRS-NSLNG-NHTNGVAIDGTLDN-NNRRVGDTNTHMDI-SA-KKTD
Ta_ROD1         ----MSTKTVVPLRRRS-KPLNG-NHTNGVAIDGSLDDDHNRRIGSVNSQMDN-IA-KKTD
Ta_ROD1_mutant  ----MSTKTVVPLRRRS-KPLNG-NHTNGVAIDGSLDDDHNRRIGSVNSQMDN-IA-KKTD
                                      :*

Os_ROD1         GGGVGGGGEVGGWRRPEW---CSAAGVAGVLRRHPAAAAFGCGLLLFMAVEYTIPMVPPA
Sl_ROD1         KKRPPSEFGDSGWLRNTFFMRLTARDVFGVVKNHPIPCIFATTLLFFMGVEYTLHMVPSS
Gm_ROD1         NG-AMGKPSSSKHSCGASFMKWTVADAVHVVTHHWMPCLFALGLLFFMAVEYTLLMVPPS
At_ROD1         NGYANGVGG-GGWRSKASFTTWTARDIVYVVRYHWIPCMFAAGLLFFMGVEYTLQMIPAR
Ta_ROD1         DGYANGGGGGGGGKSKASFMTWTARDVVYVARYHWIPCLFAVGVLFFTGVEYTLQMIPAR
Ta_ROD1_mutant  DGYANGGGGGGGGKSKASFMTWTARDVVYVARYHWIPCLFAVGVLFFTGVEYTLQMIPAR
                  .     .          :..  *    *  .  *.  ;*;* .****; *;*

Os_ROD1         APPVDLGFAATAALHAGIAARPWLNSLLAALNTVFVAMQAAYILWAILGEGRPRAAVAAM
Sl_ROD1         SPPFDLGFVATRPLHRLLDSKPALNTVLAGLNTGFVGMQMVYIVWAFLIEGRPRATIATL
Gm_ROD1         SPPFDLGFIATRSLHALLESSPNLNTLFAGLNTVFVGMQTSYILWTWLIEGRPRATISAL
At_ROD1         SEPFDLGFVVTRSLNRVLASSPDLNTVLAALNTVFVGMQTTYIVWTWLVEGRARATIAAL
Ta_ROD1         SEPFDIGFVATRSLNRVLANSPDLNTVLAALNTVFVGMQTTYIVWTWLMEGRPRATISAC
Ta_ROD1_mutant  SEPFDIGFVATRSLNRVLANSPDLNTVLAALNTVFVGMQTTYIVWTWLMEGRPRATISAC
                 : *.*:** .*  *:   :   * **;;:*,*** **.**   **;*; * *** **;::

Os_ROD1         MMFTCRGALGCATQLPLPAEFLGSGMDFPVGNVSFFLFFSGHVAGAVIAAEDMRRAGRRG
Sl_ROD1         FMFTCRGILGYSTQLPLPEDFLGSGADFPVGNVSFFLFYSGHVAASVIASLDMKRMQRWK
Gm_ROD1         FMFTCRGILGYSTQLPLPQGFLGSGVDFPVGNVSFFLFFSGHVAGSVIASLDMRRMQRWE
At_ROD1         FMFTCRGILGYSTQLPLPQDFLGSGVDFPVGNVSFFLFFSGHVAGSMIASLDMRRMQRLR
Ta_ROD1         FMFTCRGILGYSTQLPLPQDFLGSGVDFPVGNVSFFLFYSGHVAGSMIASLDMRRMQRMR
Ta_ROD1_mutant  FMFTCRGILGYSTQLPLPQDFLGSGVDFPVGNVSFFLFYSGHVAGSMIASLDIRRMQRMR
                 ;****** **  ;******   ***** *************;*****.;;**;  *;;* *

Os_ROD1         MARLYDALNLLQGVRLLACRGHYTIDLAVGVGAGLLFDMLAGRYLDGKNTVDGGAAVAPG
Sl_ROD1         LSYLFDTLNVLQTVRLLSTRGHYTIDLAVGVGAGILFDSLSGKYEEKRKKELLAGSPDGS
Gm_ROD1         LAWTFDVLNVLQAVRLLGTRGHYTIDLAVGVGAGILFDSLAGKYEDSKRNGALKHNLIA-
At_ROD1         LAMVFDILNVLQSIRLLGTRGHYTIDLAVGVGAGILFDSLAGKYEEMMSKR---H-LGTG
Ta_ROD1         LAMLFDILNVLQSIRLLGTRGHYTIDLAVGVGAGILFDSFAGKYEEMISKR---HNLVNG
Ta_ROD1_mutant  LAMLFDILNVLQSIRLLGTRGHYTIDLAVGVGAGILFDSFAGKYEEMISKR---HNLVNG
                ::   ;* **;**  ;*** .**************;*** ;;*;* ;    .

Os_ROD1         SRCCSCHKALLSQ-----------
Sl_ROD1         TNGAFHNSKLHENGEYLSVSAD
Gm_ROD1         ------------------------
At_ROD1         F-SLISKDSLVN-----------
Ta_ROD1         F-GLISKDSLVN-----------
Ta_ROD1_mutant  F-GLISKDSLVN-----------
```

FIG. 6C

SEQUENCE LISTING

```
<160> NUMBER OF SEQ ID NOS: 26

<210> SEQ ID NO 1
<211> LENGTH: 5019
<212> TYPE: DNA
<213> ORGANISM: Thlaspi arvense

<400> SEQUENCE: 1
atgggtgatg ttgaaattcc caattggcta aaagccttgc ctttggcacc tgtctttaga      60
cctacggaca ccgaattcgc agatcctatc gcgtatatat cgaaaatcga gaaagaggcc     120
agtgcttttg ggatctgcaa gatcattcct cctttaccca agccgtcgaa aaagtatgtt     180
ttctacaact tgaacaagtc tcttttgagg tgtcctgaat tggcttcgga tgtagacatt     240
tcgaaagtgt gtcaagagga tagagctgtg ttcaccacta ggcagcaaga gttagggcag     300
gctgtaaaac gaaagaaagg aggagagagc agtaagagca attctcaaag gagtggcgtt     360
aagcaggtgt ggcaaagtgg aggcgtgtac acgttggagc agttcgaatc taagtcaaaa     420
actttctaca aaagccagtt aggaaccaca aaagaagtgc caccggttgt ggttgaggca     480
ttgttctgga aagcagcttt agagaagcct atatacatag agtatgcaaa tgatgtgcct     540
ggctcggctt tcggtgaacc agagggtcat ttcaggcatt tcggcagag aaagaggaga      600 gggagaggat tttatcagag gaaggcagag gtcagtgaag acagcggagt agaaaacggg     660
acgaatagtc aagaaccaac ctgcaagaat ggtgagaaaa cattgcctga ggtagcaaag     720
```

```
gcatctcttg cttctccgag tttattatct caggatccgt ccaagcagaa gaacatggat    780
attgttgatg aaatggaagg tactgcaggc tggaagctct ccaacagttc atggaacctt    840
cagatgattg cacgttcacc tggatctgtt acacgcttca tgccagatga catccctggt    900
gtcacatctc ccatggttta tatcggtatg ttgttcagct ggtttgcctg gcacgttgag    960
gaccatgagc ttcacagtat gaattacctt cacactggct cgccaaagac gtggtacgct   1020
gtccctggtg ttattatgcatt tgactttgaa gaggttatcc gcaaaaattc gtatggcaga   1080
aacattgatc aactgggtac gttctttctg aaaagtactg ctaaatatga tatactgttt   1140
ctgtttatat agaaatgttt cgttggtgta atacatcata catgtgagaa atgagatttc   1200
ctagaatgat taccgcatcc atatttttct ttactagcac cttttttttt tgctttgtaa   1260
gtgaaatgtg gctgacattg actatgatat gacgagagt tgtactcttg ggaaattgcg    1320
ttaggactta ttgctttaag gttattatga tagatatgag acgttgcaac acttcttatg    1380
aaatgcattg tccttctgtt tctcattgac tcttagctgt tctttgtcac tttcagctgc   1440
tctcacccaa ctaggcgaaa agacaactct tgtatcacct gagatgataa ttgcatctga   1500
cattccctgc tgtaggtagg ccttttaatt ttatttgaac tttcacttct gttatgtgga   1560
gatgtgaggc agtttgtgtt ttcttataac tacgccaagc tctgctatat ctattttgt    1620 tttcccacgt aggttggtac agaatcctgg tgaatttgtt gtgacttttc cgaggtctta   1680
tcatgtagga ttcagccacg gtaaaaatgc ttttttttctt caaacattct taagtctttg   1740
tgactttact ttggtcgtcc cattttgcac tcttcaaagt gtgtgagaaa atgtgaaaat   1800
tcaaaattca aaattgagta aagctttgga gaaaaatgag tgttttacga cagagcataa   1860
ggtgaggatt gatcttctaa ttaggagaat gaagaaccaa atttctatta agtagtagtt   1920
atataagttg catagtaaaa gcggatagtt tggcttcgat taggaataca aattgcaata   1980 ttttttttcag aatccttaac taagcagaat taatttaacg ttttaaaggt tttaactgtg   2040
gggaagccgc taattttgga actccacaat ggctcaacgt agctaaggaa gctgctgtgc   2100
gacgggcagc catgaattat cttcccatgc tgtcccatca gcagctgcta tatctcttga   2160
ccatgtcctt tgtttcaagg caaatttcca tggcctcttt gtacatagaa ccctttttctg   2220 ctggaacctg ttaatcctca tattcttgta aatattaaaa ttttcagagt gccacgatca   2280
ttactaccag gtggtcgtag ctcccgactg agagatcgtc agagagaaga aagggagttc   2340
cttgtgaaaa aagcttttgt agaagatata ctgaacgaaa acaagaattt atctgttctt   2400
catcgagaac cgggatttcg tttggtgatg tgggaccctg atttactccc gcgtcatagt   2460
gtacatggtc ttgtaactgt tggggggtgct gctgtttcat ctccagcaga gggaaaaaat   2520
gaacttgagg agaagaataa agagaagact actcttttag aggaattgag tttgttcatg   2580
gagaagctga aagatgtata ctacgacgat gatgatggtc tgcttaatga tttccaggtt   2640
gattctggaa ccttggcatg tgtggcgtgt ggcgttcttg gcttcccctt tatgtctgtg   2700
gtacagcctt ctgaaaatgc attaaatgat cttttcagaga gacgaggaga gataggtaac   2760
agaccctcat tttttttaacc aaactatgaa ctacaccatc ttcgtttgaa gcctgttaat   2820
tgtgcttcta tctattctac agatggtcag gaaattacgg cactgttgtc agaaaagtct   2880
gactgtgaat ggaacatgtc ctccaggtat ataagacctc gcattttctg cctcgaacac   2940
actattgagc tccagagact gctggagtca cgaggtggac tgaagttcct tgtaatttgc   3000
cataaaggta agtacgcgtc atttgctatt aaattcgatg ccaaagagaa tattttgatc   3060
```

| | |
|---|---|
| attctgcttt taactttttt tggaattgtt gcagactttc aaaaatttaa ggcatatgcg | 3120 |
| gctatagtgg cagaggaagt taaagtccct ttcagctatg atgatatcct gttagagagt | 3180 |
| gcatctaaag aagagttgag tctgattgat cttgcaattg aagatgaaga aaacaacgaa | 3240 |
| catggcgtag actggacctc aaaacttggt atcaatttac ggtactgtgt taaagtgagg | 3300 |
| aaaaattccc cttctacgaa aattcagcat gcactgtcgc taggtggctt gttctccgat | 3360 |
| acaaaccaca tgctagatat gtcaactatc aaatggctgc agagaaaatc acgctcaaaa | 3420 |
| gccaaaccca gttgtacctc aagcttcaca cctcgtgaac atcttgaagt aaaagtagac | 3480 |
| agaaaattag gggagaagga aaagttgaa tcccaagccg aagaaaagga agaaaagatc | 3540 |
| atccagtact cgagaaagaa aaagttgaag cccaagcctt ctgaagaacg aagtcaggaa | 3600 |
| ctaactatct cagctaaatc agaagatttt gaaaacacat gcaacacact tgccaaaagg | 3660 |
| tcacatcatc atggggcaat gcattctgat atgaacaatg aaattggaga ttttgggagg | 3720 |
| aatggggtat ccttttcaga aaatcattgt agctcacctt tcactggggc acgcggacaa | 3780 |
| gaacatccca agatcattat caagtttggc tcagcattac atgggaatat tacaagcagt | 3840 |
| tctagtttgg tgaatggaat ctctgctgac ctaacttccg taaccagaga gcaccaagga | 3900 |
| cactctatga ccagcaataa taatgggtcg aactcaagta atcatgatgg cccaataaag | 3960 |
| ctgtctggtg agcatgtcag tgacgtgtct gtacgtgatg ttgatgaagc ggttgaaatg | 4020 |
| agcgaccaag agttcgaaga actgaggtct accgtcacta acattgagga ggaacagcaa | 4080 |
| tcagagatgg tgagaccaac cgcacttcag gtggagggag aggaatctat gtgtacgaga | 4140 |
| gaaatcttga gctctgaaga tattatgcac actgagcagc agcaagagca aactcaactg | 4200 |
| ggtttagaag ttcctgaaac tgacattgcc agtgagaaca tagttgtgga catgatccat | 4260 |
| gatgatgaac ctctgcaaac tagggatata ttaagttcaa gcaacggtga tcaagcttct | 4320 |
| tcaaatggct tgcaagctct agataatgaa cttagcatgg agagcgaagt tgcaagctca | 4380 |
| gaaaacaccg aggttataga ggcgtcgccc aattctatta tgcgagaagc aaataagaag | 4440 |
| cggagaatag aatcagagtc tgagacaaat gataatccag atggtagcat tggtttcata | 4500 |
| aggagtcctt gtgaagggtt gaggtcaagg ggtaggagga gagtgacgcg tgaagcttca | 4560 |
| gtcagtctca ctgaaacgag cgatgaagag aagaaacccg ctgcgaaaag gttcaagaaa | 4620 |
| actccaaaga ctcgctcggg gagtcatcac caagaagact ccacgacaag tcaccacaac | 4680 |
| cgttgtaacc tagagggatg caagatgact ttcaagagta aagcagagtt acaagctcac | 4740 |
| caaagaaacc gctgcgcaca tgaagggtgt ggaaaaaaat tcagggctca caaatatctg | 4800 |
| gtgcttcatc aacgtgttca taacgatgat agaccttttg tgtgctcttg gaaaggatgt | 4860 |
| tccatgactt tcaaatggcc atgggcgagg accgagcatt tgcgtctgca cacgggagag | 4920 |
| cgaccataca aatgcaaggt cgatggatgt ggaatgtcgt ttaggtttgt gtcggattac | 4980 |
| agccgccata gacggaaaaa ggggcattat gtgacatag | 5019 |

<210> SEQ ID NO 2
<211> LENGTH: 1330
<212> TYPE: PRT
<213> ORGANISM: Thlaspi arvense

<400> SEQUENCE: 2

Met Gly Asp Val Glu Ile Pro Asn Trp Leu Lys Ala Leu Pro Leu Ala
1               5                   10                  15

Pro Val Phe Arg Pro Thr Asp Thr Glu Phe Ala Asp Pro Ile Ala Tyr
            20                  25                  30

```
Ile Ser Lys Ile Glu Lys Glu Ala Ser Ala Phe Gly Ile Cys Lys Ile
        35                  40                  45

Ile Pro Pro Leu Pro Lys Pro Ser Lys Lys Tyr Val Phe Tyr Asn Leu
50                  55                  60

Asn Lys Ser Leu Leu Arg Cys Pro Glu Leu Ala Ser Asp Val Asp Ile
65                  70                  75                  80

Ser Lys Val Cys Gln Glu Asp Arg Ala Val Phe Thr Thr Arg Gln Gln
                85                  90                  95

Glu Leu Gly Gln Ala Val Lys Arg Lys Lys Gly Gly Glu Ser Ser Lys
                100                 105                 110

Ser Asn Ser Gln Arg Ser Gly Val Lys Gln Val Trp Gln Ser Gly Gly
            115                 120                 125

Val Tyr Thr Leu Glu Gln Phe Glu Ser Lys Ser Lys Thr Phe Tyr Lys
        130                 135                 140

Ser Gln Leu Gly Thr Thr Lys Glu Val Pro Pro Val Val Glu Ala
145                 150                 155                 160

Leu Phe Trp Lys Ala Ala Leu Glu Lys Pro Ile Tyr Ile Glu Tyr Ala
                165                 170                 175

Asn Asp Val Pro Gly Ser Ala Phe Gly Glu Pro Glu Gly His Phe Arg
            180                 185                 190

His Phe Arg Gln Arg Lys Arg Arg Gly Arg Gly Phe Tyr Gln Arg Lys
        195                 200                 205

Ala Glu Val Ser Glu Asp Ser Gly Val Glu Asn Gly Thr Asn Ser Gln
    210                 215                 220

Glu Pro Thr Cys Lys Asn Gly Glu Lys Thr Leu Pro Glu Val Ala Lys
225                 230                 235                 240

Ala Ser Leu Ala Ser Pro Ser Leu Leu Ser Gln Asp Pro Ser Lys Gln
                245                 250                 255

Lys Asn Met Asp Ile Val Asp Glu Met Glu Gly Thr Ala Gly Trp Lys
            260                 265                 270

Leu Ser Asn Ser Ser Trp Asn Leu Gln Met Ile Ala Arg Ser Pro Gly
        275                 280                 285

Ser Val Thr Arg Phe Met Pro Asp Asp Ile Pro Gly Val Thr Ser Pro
    290                 295                 300

Met Val Tyr Ile Gly Met Leu Phe Ser Trp Phe Ala Trp His Val Glu
305                 310                 315                 320

Asp His Glu Leu His Ser Met Asn Tyr Leu His Thr Gly Ser Pro Lys
                325                 330                 335

Thr Trp Tyr Ala Val Pro Gly Asp Tyr Ala Phe Asp Phe Glu Glu Val
            340                 345                 350

Ile Arg Lys Asn Ser Tyr Gly Arg Asn Ile Asp Gln Leu Ala Ala Leu
        355                 360                 365

Thr Gln Leu Gly Glu Lys Thr Thr Leu Val Ser Pro Glu Met Ile Ile
    370                 375                 380

Ala Ser Asp Ile Pro Cys Cys Arg Leu Val Gln Asn Pro Gly Glu Phe
385                 390                 395                 400

Val Val Thr Phe Pro Arg Ser Tyr His Val Gly Phe Ser His Gly Phe
                405                 410                 415

Asn Cys Gly Glu Ala Ala Asn Phe Gly Thr Pro Gln Trp Leu Asn Val
            420                 425                 430

Ala Lys Glu Ala Ala Val Arg Arg Ala Ala Met Asn Tyr Leu Pro Met
        435                 440                 445
```

```
Leu Ser His Gln Gln Leu Leu Tyr Leu Leu Thr Met Ser Phe Val Ser
450                     455                     460

Arg Gln Ile Ser Met Ala Ser Leu Val Pro Arg Ser Leu Leu Pro Gly
465                     470                     475                 480

Gly Arg Ser Ser Arg Leu Arg Asp Arg Gln Arg Glu Glu Arg Glu Phe
                    485                     490                     495

Leu Val Lys Lys Ala Phe Val Glu Asp Ile Leu Asn Glu Asn Lys Asn
                500                     505                     510

Leu Ser Val Leu His Arg Glu Pro Gly Phe Arg Leu Val Met Trp Asp
                515                     520                     525

Pro Asp Leu Leu Pro Arg His Ser Val His Gly Leu Val Thr Val Gly
530                     535                     540

Gly Ala Ala Val Ser Ser Pro Ala Glu Gly Lys Asn Glu Leu Glu Glu
545                     550                     555                 560

Lys Asn Lys Glu Lys Thr Thr Leu Leu Glu Glu Leu Ser Leu Phe Met
                565                     570                     575

Glu Lys Leu Lys Asp Val Tyr Tyr Asp Asp Asp Gly Leu Leu Asn
                580                     585                     590

Asp Phe Gln Val Asp Ser Gly Thr Leu Ala Cys Val Ala Cys Gly Val
                595                     600                     605

Leu Gly Phe Pro Phe Met Ser Val Val Gln Pro Ser Glu Asn Ala Leu
610                     615                     620

Asn Asp Leu Ser Glu Arg Arg Gly Glu Ile Asp Gly Gln Glu Ile Thr
625                     630                     635                 640

Ala Leu Leu Ser Glu Lys Ser Asp Cys Glu Trp Asn Met Ser Ser Arg
                645                     650                     655

Tyr Ile Arg Pro Arg Ile Phe Cys Leu Glu His Thr Ile Glu Leu Gln
                660                     665                     670

Arg Leu Leu Glu Ser Arg Gly Gly Leu Lys Phe Leu Val Ile Cys His
                675                     680                     685

Lys Asp Phe Gln Lys Phe Lys Ala Tyr Ala Ala Ile Val Ala Glu Glu
690                     695                     700

Val Lys Val Pro Phe Ser Tyr Asp Asp Ile Leu Leu Glu Ser Ala Ser
705                     710                     715                 720

Lys Glu Glu Leu Ser Leu Ile Asp Leu Ala Ile Glu Asp Glu Asn
                725                     730                     735

Asn Glu His Gly Val Asp Trp Thr Ser Lys Leu Gly Ile Asn Leu Arg
                740                     745                     750

Tyr Cys Val Lys Val Arg Lys Asn Ser Pro Ser Thr Lys Ile Gln His
                755                     760                     765

Ala Leu Ser Leu Gly Gly Leu Phe Ser Asp Thr Asn His Met Leu Asp
770                     775                     780

Met Ser Thr Ile Lys Trp Leu Gln Arg Lys Ser Arg Ser Lys Ala Lys
785                     790                     795                 800

Pro Ser Cys Thr Ser Ser Phe Thr Pro Arg Glu His Leu Glu Val Lys
                805                     810                     815

Val Asp Arg Lys Leu Gly Glu Lys Glu Lys Val Glu Ser Gln Ala Gly
                820                     825                     830

Arg Lys Glu Glu Lys Ile Ile Gln Tyr Ser Arg Lys Lys Leu Lys
                835                     840                     845

Pro Lys Pro Ser Glu Glu Arg Ser Gln Glu Leu Thr Ile Ser Ala Lys
850                     855                     860

Ser Glu Asp Phe Glu Asn Thr Cys Asn Thr Leu Ala Lys Arg Ser His
```

-continued

```
865                 870                 875                 880
His His Gly Ala Met His Ser Asp Met Asn Asn Glu Ile Gly Asp Phe
                    885                 890                 895
Gly Arg Asn Gly Val Ser Phe Ser Glu Asn His Cys Ser Ser Pro Phe
                    900                 905                 910
Thr Gly Ala Arg Gly Gln Glu His Pro Lys Ile Ile Ile Lys Phe Gly
                    915                 920                 925
Ser Ala Leu His Gly Asn Ile Thr Ser Ser Ser Leu Val Asn Gly
    930                 935                 940
Ile Ser Ala Asp Leu Thr Ser Val Thr Arg Glu His Gln Gly His Ser
945                 950                 955                 960
Met Thr Ser Asn Asn Asn Gly Ser Asn Ser Ser Asn His Asp Gly Pro
                    965                 970                 975
Ile Lys Leu Ser Gly Glu His Val Ser Asp Val Ser Val Arg Asp Val
                    980                 985                 990
Asp Glu Ala Val Glu Met Ser Asp Gln Glu Phe Glu Glu Leu Arg Ser
                    995                 1000                1005
Thr Val Thr Asn Ile Glu Glu Gln Gln Ser Glu Met Val Arg
    1010                1015                1020
Pro Thr Ala Leu Gln Val Glu Gly Glu Ser Met Cys Thr Arg
    1025                1030                1035
Glu Ile Leu Ser Ser Glu Asp Ile Met His Thr Glu Gln Gln Gln
    1040                1045                1050
Glu Gln Thr Gln Leu Gly Leu Glu Val Pro Glu Thr Asp Ile Ala
    1055                1060                1065
Ser Glu Asn Ile Val Val Asp Met Ile His Asp Glu Pro Leu
    1070                1075                1080
Ala Thr Arg Asp Ile Leu Ser Ser Ser Asn Gly Asp Gln Ala Ser
    1085                1090                1095
Ser Asn Gly Leu Gln Ala Leu Asp Asn Glu Leu Ser Met Glu Ser
    1100                1105                1110
Glu Val Ala Ser Ser Glu Asn Thr Glu Val Ile Glu Ala Ser Pro
    1115                1120                1125
Asn Ser Ile Met Arg Glu Ala Asn Lys Lys Arg Arg Ile Glu Ser
    1130                1135                1140
Glu Ser Glu Thr Asn Asp Asn Pro Asp Gly Ser Ile Gly Phe Ile
    1145                1150                1155
Arg Ser Pro Cys Glu Gly Leu Arg Ser Arg Gly Arg Arg Arg Val
    1160                1165                1170
Thr Arg Glu Ala Ser Val Ser Leu Thr Glu Thr Ser Asp Glu Glu
    1175                1180                1185
Lys Lys Pro Ala Ala Lys Arg Phe Lys Lys Thr Pro Lys Thr Arg
    1190                1195                1200
Ser Gly Ser His His Gln Glu Asp Ser Thr Thr Ser His His Asn
    1205                1210                1215
Arg Cys Asn Leu Glu Gly Cys Lys Met Thr Phe Lys Ser Lys Ala
    1220                1225                1230
Glu Leu Gln Ala His Gln Arg Asn Arg Cys Ala His Glu Gly Cys
    1235                1240                1245
Gly Lys Lys Phe Arg Ala His Lys Tyr Leu Val Leu His Gln Arg
    1250                1255                1260
Val His Asn Asp Asp Arg Pro Phe Val Cys Ser Trp Lys Gly Cys
    1265                1270                1275
```

| Ser | Met | Thr | Phe | Lys | Trp | Pro | Trp | Ala | Arg | Thr | Glu | His | Leu | Arg |
| | 1280 | | | | 1285 | | | | | 1290 | | | | |

| Leu | His | Thr | Gly | Glu | Arg | Pro | Tyr | Lys | Cys | Lys | Val | Asp | Gly | Cys |
| 1295 | | | | | 1300 | | | | | 1305 | | | | |

| Gly | Met | Ser | Phe | Arg | Phe | Val | Ser | Asp | Tyr | Ser | Arg | His | Arg | Arg |
| 1310 | | | | | 1315 | | | | | 1320 | | | | |

| Lys | Lys | Gly | His | Tyr | Val | Thr |
| 1325 | | | | | 1330 | |

<210> SEQ ID NO 3
<211> LENGTH: 5019
<212> TYPE: DNA
<213> ORGANISM: Artificial Sequence
<220> FEATURE:
<223> OTHER INFORMATION: modified pennycress ELF6 coding sequence

<400> SEQUENCE: 3

| | | | | | |
|---|---|---|---|---|---|
| atgggtgatg | ttgaaattcc | caattggcta | aaagccttgc | ctttggcacc | tgtctttaga | 60 |
| cctacggaca | ccgaattcgc | agatcctatc | gcgtatatat | cgaaaatcga | gaaagaggcc | 120 |
| agtgcttttg | ggatctgcaa | gatcattcct | cctttaccca | agccgtcgaa | aaagtatgtt | 180 |
| ttctacaact | tgaacaagtc | tcttttgagg | tgtcctgaat | tggcttcgga | tgtagacatt | 240 |
| tcgaaagtgt | gtcaagagga | tagagctgtg | ttcaccacta | ggcagcaaga | gttagggcag | 300 |
| gctgtaaaac | gaaagaaagg | aggagagagc | agtaagagca | attctcaaag | gagtggcgtt | 360 |
| aagcaggtgt | ggcaaagtgg | aggcgtgtac | acgttggagc | agttcgaatc | taagtcaaaa | 420 |
| actttctaca | aaagccagtt | aggaaccaca | aaagaagtgc | caccggttgt | ggttgaggca | 480 |
| ttgttctgga | aagcagcttt | agagaagcct | atatacatag | agtatgcaaa | tgatgtgcct | 540 |
| ggctcggctt | tcggtgaacc | agagggtcat | ttcaggcatt | ttcggcagag | aaagaggaga | 600 |
| gggagaggat | tttatcagag | gaaggcagag | gtcagtgaag | acagcggagt | agaaaacggg | 660 |
| acgaatagtc | aagaaccaac | ctgcaagaat | ggtgagaaaa | cattgcctga | ggtagcaaag | 720 |
| gcatctcttg | cttctccgag | tttattatct | caggatccgt | ccaagcagaa | gaacatggat | 780 |
| attgttgatg | aaatggaagg | tactgcaggc | tggaagctct | ccaacagttc | atggaacctt | 840 |
| cagatgattg | cacgttcacc | tggatctgtt | acacgcttca | tgccagatga | catccctggt | 900 |
| gtcacatctc | ccatggttta | tcggtatg | ttgttcagct | ggtttgcctg | gtacgttgag | 960 |
| gaccatgagc | ttcacagtat | gaattaccct | cacactggct | cgccaaagac | gtggtacgct | 1020 |
| gtccctggtg | attatgcatt | tgactttgaa | gaggttatcc | gcaaaaattc | gtatggcaga | 1080 |
| aacattgatc | aactgggtac | gttctttctg | aaaagtactg | ctaaatatga | tatactgttt | 1140 |
| ctgtttatat | agaaatgttt | cgttggtgta | atacatcata | catgtgagaa | atgagatttc | 1200 |
| ctagaatgat | taccgcatcc | atatttttct | ttactagcac | cttttttttt | tgctttgtaa | 1260 |
| gtgaaatgtg | gctgacattg | actatgatat | gacgagagtt | tgtactcttg | ggaaattgcg | 1320 |
| ttaggactta | ttgctttaag | gttattatga | tagatatgag | acgttgcaac | acttcttatg | 1380 |
| aaatgcattg | tccttctgtt | tctcattgac | tcttagctgt | tctttgtcac | tttcagctgc | 1440 |
| tctcacccaa | ctaggcgaaa | agacaactct | tgtatcacct | gagatgataa | ttgcatctga | 1500 |
| cattccctgc | tgtaggtagg | ccttttaatt | ttatttgaac | tttcacttct | gttatgtgga | 1560 |
| gatgtgaggc | agtttgtgtt | ttcttataac | tacgccaagc | tctgctatat | ctatttttgt | 1620 |
| tttcccacgt | aggttggtac | agaatcctgg | tgaatttgtt | gtgactttc | cgaggtctta | 1680 |

-continued

```
tcatgtagga ttcagccacg gtaaaaatgc tttttttctt caaacattct taagtctttg    1740
tgactttact ttggtcgtcc cattttgcac tcttcaaagt gtgtgagaaa atgtgaaaat    1800
tcaaaattca aaattgagta aagctttgga gaaaaatgag tgttttacga cagagcataa    1860
ggtgaggatt gatcttctaa ttaggagaat gaagaaccaa atttctatta agtagtagtt    1920
atataagttg catagtaaaa gcggatagtt tggcttcgat taggaataca aattgcaata    1980 ttttttttcag aatccttaac taagcagaat taatttaacg ttttaaaggt tttaactgtg    2040
gggaagccgc taattttgga actccacaat ggctcaacgt agctaaggaa gctgctgtgc    2100
gacgggcagc catgaattat cttcccatgc tgtcccatca gcagctgcta tatctcttga    2160
ccatgtcctt tgtttcaagg caaatttcca tggcctcttt gtacatagaa ccctttttctg   2220 ctggaacctg ttaatcctca tattcttgta aatattaaaa ttttcagagt gccacgatca    2280
ttactaccag gtggtcgtag ctcccgactg agagatcgtc agagagaaga aagggagttc    2340
cttgtgaaaa aagcttttgt agaagatata ctgaacgaaa acaagaattt atctgttctt    2400
catcgagaac cgggatttcg tttggtgatg tgggaccctg atttactccc gcgtcatagt    2460
gtacatggtc ttgtaactgt tgggggtgct gctgtttcat ctccagcaga gggaaaaaat    2520
gaacttgagg agaagaataa agagaagact actctttttag aggaattgag tttgttcatg   2580
gagaagctga agatgtata ctacgacgat gatgatggtc tgcttaatga tttccaggtt    2640
gattctggaa ccttggcatg tgtggcgtgt ggcgttcttg gcttcccctt tatgtctgtg    2700
gtacagcctt ctgaaaatgc attaaatgat ctttcagaga gacgaggaga gataggtaac    2760
agaccctcat ttttttaacc aaactatgaa ctacaccatc ttcgtttgaa gcctgttaat    2820
tgtgcttcta tctattctac agatggtcag gaaattacgg cactgttgtc agaaaagtct    2880
gactgtgaat ggaacatgtc ctccaggtat ataagacctc gcattttctg cctcgaacac    2940
actattgagc tccagagact gctggagtca cgaggtggac tgaagttcct tgtaatttgc    3000
cataaaggta gtacgcgtc atttgctatt aaattcgatg ccaaagagaa tattttgatc    3060
attctgcttt taactttttt tggaattgtt gcagactttc aaaaatttaa ggcatatgcg    3120
gctatagtgg cagaggaagt taaagtccct ttcagctatg atgatatcct gttagagagt    3180
gcatctaaag aagagttgag tctgattgat cttgcaattg aagatgaaga aaacaacgaa    3240
catggcgtag actggacctc aaaacttggt atcaatttac ggtactgtgt taaagtgagg    3300
aaaaattccc cttctacgaa aattcagcat gcactgtcgc taggtggctt gttctccgat    3360
acaaaccaca tgctagatat gtcaactatc aaatggctgc agagaaaatc acgctcaaaa    3420
gccaaaccca gttgtacctc aagcttcaca cctcgtgaac atcttgaagt aaaagtagac    3480
agaaaattag gggagaagga aaagttgaa tcccaagccg gaagaaagga agaaaagatc    3540
atccagtact cgagaaagaa aaagttgaag cccaagcctt ctgaagaacg aagtcaggaa    3600
ctaactatct cagctaaatc agaagatttt gaaaacacat gcaacacact tgccaaaagg    3660
tcacatcatc atggggcaat gcattctgat atgaacaatg aaattggaga ttttgggagg    3720
aatggggtat cctttttcaga aaatcattgt agctcacctt tcactggggc acgcggacaa    3780
gaacatccca agatcattat caagtttggc tcagcattac atgggaatat tacaagcagt    3840 tctagttttgg tgaatggaat ctctgctgac ctaacttccg taaccagaga gcaccaagga    3900
cactctatga ccagcaataa taatgggtcg aactcaagta atcatgatgg cccaataaag    3960
ctgtctggtg agcatgtcag tgacgtgtct gtacgtgatg ttgatgaagc ggttgaaatg    4020
agcgaccaag agttcgaaga actgaggtct accgtcacta acattgagga ggaacagcaa    4080
```

```
tcagagatgg tgagaccaac cgcacttcag gtggagggag aggaatctat gtgtacgaga    4140
gaaatcttga gctctgaaga tattatgcac actgagcagc agcaagagca aactcaactg    4200
ggtttagaag ttcctgaaac tgacattgcc agtgagaaca tagttgtgga catgatccat    4260
gatgatgaac ctctggcaac tagggatata ttaagttcaa gcaacggtga tcaagcttct    4320
tcaaatggct tgcaagctct agataatgaa cttagcatgg agagcgaagt tgcaagctca    4380
gaaaacaccg aggttataga ggcgtcgccc aattctatta tgcgagaagc aaataagaag    4440
cggagaatag aatcagagtc tgagacaaat gataatccag atggtagcat tggtttcata    4500
aggagtcctt gtgaagggtt gaggtcaagg ggtaggagga gagtgacgcg tgaagcttca    4560
gtcagtctca ctgaaacgag cgatgaagag aagaaacccg ctgcgaaaag gttcaagaaa    4620
actccaaaga ctcgctcggg gagtcatcac caagaagact ccacgacaag tcaccacaac    4680
cgttgtaacc tagagggatg caagatgact ttcaagagta aagcagagtt acaagctcac    4740
caaagaaacc gctgcgcaca tgaagggtgt ggaaaaaaat tcagggctca caaatatctg    4800
gtgcttcatc aacgtgttca taacgatgat agaccttttg tgtgctcttg gaaaggatgt    4860
tccatgactt tcaaatggcc atgggcgagg accgagcatt tgcgtctgca cacgggagag    4920
cgaccataca aatgcaaggt cgatggatgt ggaatgtcgt ttaggtttgt gtcggattac    4980
agccgccata gacggaaaaa ggggcattat gtgacatag                           5019
```

<210> SEQ ID NO 4
<211> LENGTH: 1314
<212> TYPE: PRT
<213> ORGANISM: Artificial Sequence
<220> FEATURE:
<223> OTHER INFORMATION: modified pennycress ELF6 polypeptide

<400> SEQUENCE: 4

```
Met Gly Asp Val Glu Ile Pro Asn Trp Leu Lys Ala Leu Pro Leu Ala
1               5                   10                  15

Pro Val Phe Arg Pro Thr Asp Thr Glu Phe Ala Asp Pro Ile Ala Tyr
            20                  25                  30

Ile Ser Lys Ile Glu Lys Glu Ala Ser Ala Phe Gly Ile Cys Lys Ile
        35                  40                  45

Ile Pro Pro Leu Pro Lys Pro Ser Lys Lys Tyr Val Phe Tyr Asn Leu
    50                  55                  60

Asn Lys Ser Leu Leu Arg Cys Pro Glu Leu Ala Ser Asp Val Asp Ile
65                  70                  75                  80

Ser Lys Val Cys Gln Glu Asp Arg Ala Val Phe Thr Thr Arg Gln Gln
                85                  90                  95

Glu Leu Gly Gln Ala Val Lys Arg Lys Lys Gly Gly Glu Ser Ser Lys
            100                 105                 110

Ser Asn Ser Gln Arg Ser Gly Val Lys Gln Val Trp Gln Ser Gly Gly
        115                 120                 125

Val Tyr Thr Leu Glu Gln Phe Glu Ser Lys Ser Lys Thr Phe Tyr Lys
    130                 135                 140

Ser Gln Leu Gly Thr Thr Lys Glu Val Pro Val Val Val Glu Ala
145                 150                 155                 160

Leu Phe Trp Lys Ala Ala Leu Glu Lys Pro Ile Tyr Ile Glu Tyr Ala
                165                 170                 175

Asn Asp Val Pro Gly Ser Ala Phe Gly Glu Pro Glu Gly His Phe Arg
            180                 185                 190
```

```
His Phe Arg Gln Arg Lys Arg Arg Gly Arg Gly Phe Tyr Gln Arg Lys
            195                 200                 205

Ala Glu Val Ser Glu Asp Ser Gly Val Glu Asn Gly Thr Asn Ser Gln
        210                 215                 220

Glu Pro Thr Cys Lys Asn Gly Glu Lys Thr Leu Pro Glu Val Ala Lys
225                 230                 235                 240

Ala Ser Leu Ala Ser Pro Ser Leu Leu Ser Gln Asp Pro Ser Lys Gln
                245                 250                 255

Lys Asn Met Asp Ile Val Asp Glu Met Glu Gly Thr Ala Gly Trp Lys
            260                 265                 270

Leu Ser Asn Ser Ser Trp Asn Leu Gln Met Ile Ala Arg Ser Pro Gly
        275                 280                 285

Ser Val Thr Arg Phe Met Pro Asp Asp Ile Pro Gly Val Thr Ser Pro
    290                 295                 300

Met Val Tyr Ile Gly Met Leu Phe Ser Trp Phe Ala Trp Tyr Val Glu
305                 310                 315                 320

Asp His Glu Leu His Ser Met Asn Tyr Leu His Thr Gly Ser Pro Lys
                325                 330                 335

Thr Trp Tyr Ala Val Pro Gly Asp Tyr Ala Phe Asp Phe Glu Glu Val
            340                 345                 350

Ile Arg Lys Asn Ser Tyr Gly Arg Asn Ile Asp Gln Leu Ala Ala Leu
        355                 360                 365

Thr Gln Leu Gly Glu Lys Thr Thr Leu Val Ser Pro Glu Met Ile Ile
    370                 375                 380

Ala Ser Asp Ile Pro Cys Cys Arg Leu Val Gln Asn Pro Gly Glu Phe
385                 390                 395                 400

Val Val Thr Phe Pro Arg Ser Tyr His Val Gly Phe Ser His Gly Phe
                405                 410                 415

Asn Cys Gly Glu Ala Ala Asn Phe Gly Thr Pro Gln Trp Leu Asn Val
            420                 425                 430

Ala Lys Glu Ala Ala Val Arg Arg Ala Ala Met Asn Tyr Leu Pro Met
        435                 440                 445

Leu Ser His Gln Gln Leu Leu Tyr Leu Leu Thr Met Ser Phe Val Ser
    450                 455                 460

Arg Gln Ile Ser Met Ala Ser Leu Val Pro Arg Ser Leu Leu Pro Gly
465                 470                 475                 480

Gly Arg Ser Ser Arg Leu Arg Asp Arg Gln Arg Glu Glu Arg Glu Phe
                485                 490                 495

Leu Val Lys Lys Ala Phe Val Glu Asp Ile Leu Asn Glu Asn Lys Asn
            500                 505                 510

Leu Ser Val Leu His Arg Glu Pro Gly Phe Arg Leu Val Met Trp Asp
        515                 520                 525

Pro Asp Leu Leu Pro Arg His Ser Val His Gly Leu Val Thr Val Gly
    530                 535                 540

Gly Ala Ala Val Ser Ser Pro Ala Glu Gly Lys Asn Glu Leu Glu Glu
545                 550                 555                 560

Lys Asn Lys Glu Lys Thr Thr Leu Leu Glu Glu Leu Ser Leu Phe Met
                565                 570                 575

Glu Lys Leu Lys Asp Val Tyr Tyr Asp Asp Asp Gly Leu Leu Asn
            580                 585                 590

Asp Phe Gln Val Asp Ser Gly Thr Leu Ala Cys Val Ala Cys Gly Val
        595                 600                 605

Leu Gly Phe Pro Phe Met Ser Val Val Gln Pro Ser Glu Asn Ala Leu
```

```
                610             615             620
Asn Asp Leu Ser Glu Arg Arg Gly Glu Ile Asp Gly Gln Glu Ile Thr
625             630             635             640

Ala Leu Leu Ser Glu Lys Ser Asp Cys Glu Trp Asn Met Ser Ser Arg
            645             650             655

Tyr Ile Arg Pro Arg Ile Phe Cys Leu Glu His Thr Ile Glu Leu Gln
            660             665             670

Arg Leu Leu Glu Ser Arg Gly Gly Leu Lys Phe Leu Val Ile Cys His
            675             680             685

Lys Asp Phe Gln Lys Phe Lys Ala Tyr Ala Ala Ile Val Ala Glu Glu
            690             695             700

Val Lys Val Pro Phe Ser Tyr Asp Asp Ile Leu Leu Glu Ser Ala Ser
705             710             715             720

Lys Glu Glu Leu Ser Leu Ile Asp Leu Ala Ile Glu Asp Glu Glu Asn
            725             730             735

Asn Glu His Gly Val Asp Trp Thr Ser Lys Leu Gly Ile Asn Leu Arg
            740             745             750

Tyr Cys Val Lys Val Arg Lys Asn Ser Pro Ser Thr Lys Ile Gln His
            755             760             765

Ala Leu Ser Leu Gly Gly Leu Phe Ser Asp Thr Asn His Met Leu Asp
            770             775             780

Met Ser Thr Ile Lys Trp Leu Gln Arg Lys Ser Arg Ser Lys Ala Lys
785             790             795             800

Pro Ser Cys Thr Ser Ser Phe Thr Pro Arg Glu His Leu Glu Val Lys
            805             810             815

Val Asp Arg Lys Leu Gly Glu Lys Glu Lys Val Glu Ser Gln Ala Gly
            820             825             830

Arg Lys Glu Glu Lys Ile Ile Gln Tyr Ser Arg Lys Lys Leu Lys
            835             840             845

Pro Lys Pro Ser Glu Glu Arg Ser Gln Glu Leu Thr Ile Ser Ala Lys
            850             855             860

Ser Glu Asp Phe Glu Asn Thr Cys Asn Thr Leu Ala Lys Arg Ser His
865             870             875             880

His His Gly Ala Met His Ser Asp Met Asn Asn Glu Ile Gly Asp Phe
            885             890             895

Gly Arg Asn Gly Val Ser Phe Ser Glu Asn His Cys Ser Ser Pro Phe
            900             905             910

Thr Gly Ala Arg Gly Gln Glu His Pro Lys Ile Ile Lys Phe Gly
            915             920             925

Ser Ala Leu His Gly Asn Ile Thr Ser Ser Ser Leu Val Asn Gly
930             935             940

Ile Ser Ala Asp Leu Thr Ser Val Thr Arg Ser Asn His Asp Gly Pro
945             950             955             960

Ile Lys Leu Ser Gly Glu His Val Ser Asp Val Ser Val Arg Asp Val
            965             970             975

Asp Glu Ala Val Glu Met Ser Asp Gln Glu Phe Glu Glu Leu Arg Ser
            980             985             990

Thr Val Thr Asn Ile Glu Glu Glu  Gln Gln Ser Glu Met  Val Arg Pro
            995             1000            1005

Thr Ala  Leu Gln Val Glu Gly  Glu Glu Ser Met Cys  Thr Arg Glu
        1010            1015            1020

Ile Leu  Ser Ser Glu Asp Ile  Met His Thr Glu Gln  Gln Gln Glu
        1025            1030            1035
```

Gln Thr Gln Leu Gly Leu Glu Val Pro Glu Thr Asp Ile Ala Ser
    1040            1045                1050

Glu Asn Ile Val Val Asp Met Ile His Asp Asp Glu Pro Leu Ala
    1055            1060                1065

Thr Arg Asp Ile Leu Ser Ser Ser Asn Gly Asp Gln Ala Ser Ser
    1070            1075                1080

Asn Gly Leu Gln Ala Leu Asp Asn Glu Leu Ser Met Glu Ser Glu
    1085            1090                1095

Val Ala Ser Ser Glu Asn Thr Glu Val Ile Glu Ala Ser Pro Asn
    1100            1105                1110

Ser Ile Met Arg Glu Ala Asn Lys Lys Arg Arg Ile Glu Ser Glu
    1115            1120                1125

Ser Glu Thr Asn Asp Asn Pro Asp Gly Ser Ile Gly Phe Ile Arg
    1130            1135                1140

Ser Pro Cys Glu Gly Leu Arg Ser Arg Gly Arg Arg Val Thr
    1145            1150                1155

Arg Glu Ala Ser Val Ser Leu Thr Glu Thr Ser Asp Glu Glu Lys
    1160            1165                1170

Lys Pro Ala Ala Lys Arg Phe Lys Lys Thr Pro Lys Thr Arg Ser
    1175            1180                1185

Gly Ser His His Gln Glu Asp Ser Thr Thr Ser His His Asn Arg
    1190            1195                1200

Cys Asn Leu Glu Gly Cys Lys Met Thr Phe Lys Ser Lys Ala Glu
    1205            1210                1215

Leu Gln Ala His Gln Arg Asn Arg Cys Ala His Glu Gly Cys Gly
    1220            1225                1230

Lys Lys Phe Arg Ala His Lys Tyr Leu Val Leu His Gln Arg Val
    1235            1240                1245

His Asn Asp Asp Arg Pro Phe Val Cys Ser Trp Lys Gly Cys Ser
    1250            1255                1260

Met Thr Phe Lys Trp Pro Trp Ala Arg Thr Glu His Leu Arg Leu
    1265            1270                1275

His Thr Gly Glu Arg Pro Tyr Lys Cys Lys Val Asp Gly Cys Gly
    1280            1285                1290

Met Ser Phe Arg Phe Val Ser Asp Tyr Ser Arg His Arg Arg Lys
    1295            1300                1305

Lys Gly His Tyr Val Thr
    1310

<210> SEQ ID NO 5
<211> LENGTH: 2146
<212> TYPE: DNA
<213> ORGANISM: Thlaspi arvense

<400> SEQUENCE: 5
atgtcaacta aaaccgtcgt ccctctccgt cgcagatcta agccccttaa cggaaatcac     60
actaacggcg tcgccattga cggaagcctc gacgacgacc acaaccgtcg catcggatca    120
gtaaatagcc aaatggataa cattgctaag aaaacggacg acggctacgc aaacggcgga    180
ggaggaggag gaggagggaa aagcaaggcg tcgtttatga cgtggacggc gcgtgacgtt    240
gtgtacgtgg cgaggtacca ttggataccg tgtttgttcg cggtcggggt tctgttcttc    300
acgggcgtga agtacacgct ccagatgatt cccgcgaggt ctgagccgtt cgatattggg    360
tttgtggcca cgcgctctct gaatcgcgtc ttggcaaatt caccggatct aacaccgtc     420

```
ttagccgctc taaacacggt aatttcgtac taattaattt agggtaaaaa atatagtatt    480
taataatgac tatcctcaat tcctttcatg cttcacctaa tattttgttt ttttcgttg    540 tcattaaaat cgtaataata tattgagtta gtcaaatgaa aaaacaagt ggcggtagtg    600 attggaaaca atctcagat cttttatctg tttaataagg tatttaatta tccagctgga    660
attatgctgt caagtgtcaa cacagtagta gtaacatgca atggaattc tcaatagaaa    720 aaggtcttaa ttagtataga taattagtgg acaaaaatgt agttaatgta atctctttgc    780
taagtagtta tcataatcat ctttttaaca actgccattt tgtctgtgtg tttgttttac    840
aacgaagtag tagtagaata gatcgctttt tagcttttga aagtttcgaa cccaaggaaa    900
agggacacat gggttatgag ttggagacac gatcacatgc aaacagagag attggttaaa    960
ttatcgactt tttgtagtac ttttaaaaa aaaactattt atataaaaaa catggtggat    1020
ggtggggaca ggtgttcgta gggatgcaaa cgacgtatat tgtatggaca tggttaatgg    1080
aaggacgacc acgagccacc atctcggctt gcttcatgtt tacttgtcga ggcattcttg    1140
gttactctac tcagctccct cttcctcagg ttccaatcaa cacttttctt ctatctcttt    1200
tcttaattaa ataattacc aattaactaa atgctaatca gtcgatatat catagttcca    1260
acgttttgga cgtgtgattt ccattggcca ctaccatata aaacaacaga gtctctttat    1320
tcattattca atatatattt gagtattgat attattcata gggaggtttc atttgtacta    1380
tcaataaaat ttctacaact cttggatttt ttctgctaca ttttgtagtt attttttttaa    1440 ttactttttaa aaacttgtga ataggagaga ctaaatagtag tacgtaatat gattgtatca    1500
aatgctttaa catgtgggggt ttgggttaac tatcatcatt tcatagatca ctattttgtt    1560
ttcgtttgtt acctaacttt ttgttatctt tgaaaaataa tgttccacga gttgattgac    1620
tggacataaa aatcagattc tctcactcat ttacgttcta cggttctagc cactcgtttt    1680 tttcttttttc tttctgtggt gtaacacgta gataatggat tttctatgtg tgtcgtcttg    1740
ctcaagaata ataaatgtgg ttaaaggtta aatatagctc tggaaattaa ttatctcctc    1800 ttttttttatt aaccaggatt ttctaggatc aggtgtcgat tttccggtgg gaaacgtctc    1860
gttcttcctc ttctactcgg gtcacgtcgc cggttcgatg atcgcatctt tggacatgag    1920
gagaatgcag aggatgagac tagcgatgct ttttgacatc ctcaatgtat tacaatcgat    1980
caggctgctc gggacgagag gacactacac gattgatctc gctgtcggag ttggcgctgg    2040
gattctcttt gattcattcg ccggcaagta cgaagagatg ataagcaaga gacacaattt    2100
agtcaatggt tttggtttga tttcgaaaga ctcgctagtc aattaa    2146
```

<210> SEQ ID NO 6
<211> LENGTH: 301
<212> TYPE: PRT
<213> ORGANISM: Thlaspi arvense

<400> SEQUENCE: 6

Met Ser Thr Lys Thr Val Val Pro Leu Arg Arg Ser Lys Pro Leu
1               5                   10                  15

Asn Gly Asn His Thr Asn Gly Val Ala Ile Asp Gly Ser Leu Asp Asp
            20                  25                  30

Asp His Asn Arg Arg Ile Gly Ser Val Asn Ser Gln Met Asp Asn Ile
        35                  40                  45

Ala Lys Lys Thr Asp Asp Gly Tyr Ala Asn Gly Gly Gly Gly Gly Gly
    50                  55                  60

Gly Gly Lys Ser Lys Ala Ser Phe Met Thr Trp Thr Ala Arg Asp Val
65                  70                  75                  80

Val Tyr Val Ala Arg Tyr His Trp Ile Pro Cys Leu Phe Ala Val Gly
                85                  90                  95

Val Leu Phe Phe Thr Gly Val Glu Tyr Thr Leu Gln Met Ile Pro Ala
            100                 105                 110

Arg Ser Glu Pro Phe Asp Ile Gly Phe Val Ala Thr Arg Ser Leu Asn
        115                 120                 125

Arg Val Leu Ala Asn Ser Pro Asp Leu Asn Thr Val Leu Ala Ala Leu
    130                 135                 140

Asn Thr Val Phe Val Gly Met Gln Thr Thr Tyr Ile Val Trp Thr Trp
145                 150                 155                 160

Leu Met Glu Gly Arg Pro Arg Ala Thr Ile Ser Ala Cys Phe Met Phe
                165                 170                 175

Thr Cys Arg Gly Ile Leu Gly Tyr Ser Thr Gln Leu Pro Leu Pro Gln
            180                 185                 190

Asp Phe Leu Gly Ser Gly Val Asp Phe Pro Val Gly Asn Val Ser Phe
        195                 200                 205

Phe Leu Phe Tyr Ser Gly His Val Ala Gly Ser Met Ile Ala Ser Leu
    210                 215                 220

Asp Met Arg Arg Met Gln Arg Met Arg Leu Ala Met Leu Phe Asp Ile
225                 230                 235                 240

Leu Asn Val Leu Gln Ser Ile Arg Leu Leu Gly Thr Arg Gly His Tyr
                245                 250                 255

Thr Ile Asp Leu Ala Val Gly Val Gly Ala Gly Ile Leu Phe Asp Ser
            260                 265                 270

Phe Ala Gly Lys Tyr Glu Glu Met Ile Ser Lys Arg His Asn Leu Val
        275                 280                 285

Asn Gly Phe Gly Leu Ile Ser Lys Asp Ser Leu Val Asn
    290                 295                 300

```
<210> SEQ ID NO 7
<211> LENGTH: 2146
<212> TYPE: DNA
<213> ORGANISM: Artificial Sequence
<220> FEATURE:
<223> OTHER INFORMATION: modified pennycress rod1 coding sequence

<400> SEQUENCE: 7
atgtcaacta aaccgtcgt ccctctccgt cgcagatcta agccccttaa cggaaatcac      60
actaacggcg tcgccattga cggaagcctc gacgacgacc acaaccgtcg catcggatca    120
gtaaatagcc aaatggataa cattgctaag aaaacggacg acggctacgc aaacggcgga    180
ggaggaggag gaggagggaa aagcaaggcg tcgtttatga cgtggacggc ggtgacgtt     240 gtgtacgtgg cgaggtacca ttggataccg tgtttgttcg cggtcggggt tctgttcttc    300
acgggcgtgg agtacacgct ccagatgatt cccgcgaggt ctgagccgtt cgatattggg    360
tttgtggcca cgcgctctct gaatcgcgtc ttggcaaatt caccggatct taacaccgtc    420
ttagccgctc taaacacggt aatttcgtac taattaattt agggtaaaaa atatagtatt    480
taataatgac tatcctcaat tcctttcatg cttcacctaa tattttgttt ttttcgttg     540 tcattaaaat cgtaataata tattgagtta gtcaaatgaa aaaacaagt ggcggtagtg     600 attggaaaca aatctcagat ctttatctg tttaataagg tatttaatta tccagctgga    660
attatgctgt caagtgtcaa cacagtagta gtaacatgca atggaatttc tcaatagaaa    720
```

```
aaggtcttaa ttagtataga taattagtgg acaaaaatgt agttaatgta atctctttgc    780
taagtagtta tcataatcat cttttaaca actgccattt tgtctgtgtg tttgttttac     840
aacgaagtag tagtagaata gatcgctttt tagcttttga agtttcgaa cccaaggaaa     900
agggacacat gggttatgag ttggagacac gatcacatgc aaacagagag attggttaaa   960
ttatcgactt tttgtagtac ttttaaaaa aaactattt atataaaaa catggtggat     1020
ggtggggaca ggtgttcgta gggatgcaaa cgacgtatat tgtatggaca tggttaatgg   1080
aaggacgacc acgagccacc atctcggctt gcttcatgtt tacttgtcga ggcattcttg   1140
gttactctac tcagctccct cttcctcagg ttccaatcaa cacttttctt ctatctcttt   1200
tcttaattaa ataattacc aattaactaa atgctaatca gtcgatatat catagttcca   1260
acgttttgga cgtgtgattt ccattggcca ctaccatata aaacaacaga gtctctttat   1320
tcattattca atatatattt gagtattgat attattcata gggaggtttc atttgtacta   1380
tcaataaaat ttctacaact cttggatttt ttctgctaca ttttgtagtt attttttaa   1440
ttactttaa aaacttgtga ataggagaga ctaatagtag tacgtaatat gattgtatca   1500
aatgctttaa catgtggggt ttgggttaac tatcatcatt tcatagatca ctattttgtt   1560
ttcgtttgtt acctaacttt ttgttatctt tgaaaaataa tgttccacga gttgattgac   1620
tggacataaa aatcgattc tctcactcat ttacgttcta cggttctagc cactcgtttt   1680
tttcttttc tttctgtggt gtaacacgta gataatggat tttctatgtg tgtcgtcttg   1740
ctcaagaata taaatgtgg ttaaaggtta aatatagctc tggaaattaa ttatctcctc   1800
ttttttatt aaccaggatt ttctaggatc aggtgtcgat tttccggtgg gaaacgtctc   1860
gttcttcctc ttctactcgg gtcacgtcgc cggttcgatg atcgcatctt tggacataag   1920
gagaatgcag aggatgagac tagcgatgct ttttgacatc ctcaatgtat tacaatcgat   1980
caggctgctc gggacgagag gacactacac gattgatctc gctgtcggag ttggcgctgg   2040
gattctcttt gattcattcg ccggcaagta cgaagagatg ataagcaaga gacacaattt   2100
agtcaatggt tttggtttga tttcgaaaga ctcgctagtc aattaa                   2146
```

<210> SEQ ID NO 8
<211> LENGTH: 301
<212> TYPE: PRT
<213> ORGANISM: Artificial Sequence
<220> FEATURE:
<223> OTHER INFORMATION: modified pennycress rod1 polypeptide

<400> SEQUENCE: 8

```
Met Ser Thr Lys Thr Val Val Pro Leu Arg Arg Ser Lys Pro Leu
1               5                   10                  15

Asn Gly Asn His Thr Asn Gly Val Ala Ile Asp Gly Ser Leu Asp Asp
            20                  25                  30

Asp His Asn Arg Arg Ile Gly Ser Val Asn Ser Gln Met Asp Asn Ile
        35                  40                  45

Ala Lys Lys Thr Asp Asp Gly Tyr Ala Asn Gly Gly Gly Gly Gly
    50                  55                  60

Gly Gly Lys Ser Lys Ala Ser Phe Met Thr Trp Thr Ala Arg Asp Val
65                  70                  75                  80

Val Tyr Val Ala Arg Tyr His Trp Ile Pro Cys Leu Phe Ala Val Gly
                85                  90                  95

Val Leu Phe Phe Thr Gly Val Glu Tyr Thr Leu Gln Met Ile Pro Ala
                100                 105                 110
```

```
Arg Ser Glu Pro Phe Asp Ile Gly Phe Val Ala Thr Arg Ser Leu Asn
            115                 120                 125

Arg Val Leu Ala Asn Ser Pro Asp Leu Asn Thr Val Leu Ala Ala Leu
        130                 135                 140

Asn Thr Val Phe Val Gly Met Gln Thr Thr Tyr Ile Val Trp Thr Trp
145                 150                 155                 160

Leu Met Glu Gly Arg Pro Arg Ala Thr Ile Ser Ala Cys Phe Met Phe
                165                 170                 175

Thr Cys Arg Gly Ile Leu Gly Tyr Ser Thr Gln Leu Pro Leu Pro Gln
            180                 185                 190

Asp Phe Leu Gly Ser Gly Val Asp Phe Pro Val Gly Asn Val Ser Phe
        195                 200                 205

Phe Leu Phe Tyr Ser Gly His Val Ala Gly Ser Met Ile Ala Ser Leu
    210                 215                 220

Asp Ile Arg Arg Met Gln Arg Met Arg Leu Ala Met Leu Phe Asp Ile
225                 230                 235                 240

Leu Asn Val Leu Gln Ser Ile Arg Leu Leu Gly Thr Arg Gly His Tyr
                245                 250                 255

Thr Ile Asp Leu Ala Val Gly Val Gly Ala Gly Ile Leu Phe Asp Ser
            260                 265                 270

Phe Ala Gly Lys Tyr Glu Glu Met Ile Ser Lys Arg His Asn Leu Val
        275                 280                 285

Asn Gly Phe Gly Leu Ile Ser Lys Asp Ser Leu Val Asn
    290                 295                 300

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 9
gtgtgtcgtc ttgctcaaga                                                 20

<210> SEQ ID NO 10
<211> LENGTH: 24
<212> TYPE: DNA
<213> ORGANISM: Artificial Sequence
<220> FEATURE:
<223> OTHER INFORMATION: synthetic oligonucleotide primer

<400> SEQUENCE: 10
gttcaagtaa ttaacagtat attc                                            24

<210> SEQ ID NO 11
<211> LENGTH: 1339
<212> TYPE: PRT
<213> ORGANISM: Arabidopsis thaliana

<400> SEQUENCE: 11

Met Gly Asn Val Glu Ile Pro Asn Trp Leu Lys Ala Leu Pro Leu Ala
1               5                   10                  15

Pro Val Phe Arg Pro Thr Asp Thr Glu Phe Ala Asp Pro Ile Ala Tyr
            20                  25                  30

Ile Ser Lys Ile Glu Lys Glu Ala Ser Ala Phe Gly Ile Cys Lys Ile
        35                  40                  45

Ile Pro Pro Leu Pro Lys Pro Ser Lys Lys Tyr Val Phe Tyr Asn Leu
    50                  55                  60
```

```
Asn Lys Ser Leu Leu Lys Cys Pro Glu Leu Val Ser Asp Val Asp Ile
 65                  70                  75                  80

Ser Lys Val Cys Lys Glu Asp Arg Ala Val Phe Thr Thr Arg Gln Gln
                 85                  90                  95

Glu Leu Gly Gln Thr Val Lys Lys Asn Lys Gly Glu Lys Gly Lys Ser
            100                 105                 110

Asn Ser Gln Arg Ser Gly Val Lys Gln Val Trp Gln Ser Gly Gly Val
        115                 120                 125

Tyr Thr Leu Asp Gln Phe Glu Ala Lys Ser Lys Ala Phe Tyr Lys Thr
    130                 135                 140

Gln Leu Gly Thr Val Lys Glu Leu Ala Pro Val Val Ile Glu Ala Leu
145                 150                 155                 160

Phe Trp Lys Ala Ala Leu Glu Lys Pro Ile Tyr Ile Glu Tyr Ala Asn
                165                 170                 175

Asp Val Pro Gly Ser Ala Phe Gly Pro Glu Asp His Phe Arg His
            180                 185                 190

Phe Arg Gln Arg Lys Arg Gly Arg Gly Phe Tyr Gln Arg Lys Thr
        195                 200                 205

Glu Asn Asn Asp Pro Ser Gly Lys Asn Gly Glu Lys Ser Ser Pro Glu
    210                 215                 220

Val Glu Lys Ala Pro Leu Ala Ser Thr Ser Leu Ser Ser Gln Asp Ser
225                 230                 235                 240

Ser Lys Gln Lys Asn Met Asp Ile Val Asp Glu Met Glu Gly Thr Ala
                245                 250                 255

Gly Trp Lys Leu Ser Asn Ser Ser Trp Asn Leu Gln Met Ala Arg Ser
            260                 265                 270

Pro Gly Ser Val Thr Arg Phe Met Pro Asp Asp Ile Pro Gly Val Thr
        275                 280                 285

Ser Pro Met Val Tyr Ile Gly Met Leu Phe Ser Trp Phe Ala Trp His
    290                 295                 300

Val Glu Asp His Glu Leu His Ser Met Asn Tyr Leu His Thr Gly Ser
305                 310                 315                 320

Pro Lys Thr Trp Tyr Ala Val Pro Cys Asp Tyr Ala Leu Asp Phe Glu
                325                 330                 335

Glu Val Ile Arg Lys Asn Ser Tyr Gly Arg Asn Ile Asp Gln Leu Ala
            340                 345                 350

Ala Leu Thr Gln Leu Gly Glu Lys Thr Thr Leu Val Ser Pro Glu Met
        355                 360                 365

Val Ala Ser Gly Ile Pro Cys Cys Arg Leu Val Gln Asn Pro Gly Glu
    370                 375                 380

Phe Val Val Thr Phe Pro Arg Ser Tyr His Val Gly Phe Ser His Gly
385                 390                 395                 400

Phe Asn Cys Gly Glu Ala Ala Asn Phe Gly Thr Pro Gln Trp Leu Asn
                405                 410                 415

Val Ala Lys Glu Ala Ala Val Arg Arg Ala Ala Met Asn Tyr Leu Pro
            420                 425                 430

Met Leu Ser His His Gln Gln Leu Leu Tyr Leu Leu Thr Met Ser Phe
        435                 440                 445

Val Ser Arg Val Pro Arg Ser Leu Leu Pro Gly Gly Arg Ser Ser Arg
    450                 455                 460

Leu Arg Asp Arg Gln Arg Glu Glu Arg Glu Phe Leu Val Lys Arg Ala
465                 470                 475                 480
```

```
Phe Val Glu Asp Ile Leu Asn Glu Asn Lys Asn Leu Ser Val Leu Leu
            485                 490                 495
Arg Glu Pro Gly Ser Arg Leu Val Met Trp Asp Pro Asp Leu Leu Pro
            500                 505                 510
Arg His Ser Ala Leu Ala Leu Ala Ala Gly Val Ala Gly Ala Ser
        515                 520                 525
Ala Val Ser Pro Pro Ala Val Ala Lys Lys Glu Leu Glu Glu Gly His
530                 535                 540
Ser Glu Leu Gln Asn Lys Glu Lys Thr Ser Leu Leu Glu Leu Ser
545                 550                 555                 560
Leu Phe Met Glu Lys Leu Asn Asp Val Tyr Tyr Asp Asp Asp Gly
            565                 570                 575
Leu Leu Asn Asp Phe Gln Val Asp Thr Gly Thr Leu Pro Cys Val Ala
            580                 585                 590
Cys Gly Val Leu Gly Phe Pro Phe Met Ser Val Val Gln Pro Ser Glu
        595                 600                 605
Lys Ala Leu Lys Asp Leu Ser Glu Arg Gln Gly Glu Thr Asp Ala Gln
        610                 615                 620
Glu Ile Met Thr Leu Ser Ser Glu Lys Ser Asp Cys Glu Trp Lys Thr
625                 630                 635                 640
Ser Ser Arg Tyr Ile Arg Pro Arg Ile Phe Cys Leu Glu His Thr Ile
            645                 650                 655
Glu Leu Gln Arg Leu Leu Gln Ser Arg Gly Gly Leu Lys Phe Leu Val
            660                 665                 670
Ile Cys His Lys Asp Phe Gln Lys Phe Lys Ala His Ala Ala Ile Val
        675                 680                 685
Ala Glu Glu Val Lys Val Pro Phe Ser Tyr Asp Asp Val Leu Leu Glu
        690                 695                 700
Ser Ala Ser Gln Glu Glu Leu Ser Leu Ile Asp Leu Ala Ile Glu Asp
705                 710                 715                 720
Glu Glu Lys Tyr Glu His Ser Val Asp Trp Thr Ser Glu Leu Gly Ile
            725                 730                 735
Asn Leu Arg Tyr Cys Val Lys Val Arg Lys Asn Ser Pro Thr Lys Lys
            740                 745                 750
Ile Gln His Ala Leu Ser Leu Gly Gly Leu Phe Ser Asp Thr Ser Gln
        755                 760                 765
Met Leu Asp Phe Thr Thr Ile Arg Trp Leu Gln Arg Lys Ser Arg Ser
        770                 775                 780
Lys Ala Lys Pro Ser Ser Thr Ser Ser Phe Thr Pro Cys Glu His Leu
785                 790                 795                 800
Glu Val Lys Ala Asp Gly Lys Leu Arg Asp Asn Leu Asp Ser Gln Thr
            805                 810                 815
Gly Lys Lys Glu Glu Lys Ile Ile Gln Tyr Ser Arg Lys Lys Lys Leu
            820                 825                 830
Asn Pro Lys Pro Ser Ala Glu Gln Val Gln Glu Leu Ala Thr Leu Ala
        835                 840                 845
Lys Ser Lys Asp Phe Asp Lys Thr Cys Lys Asn Phe Ser Ser Arg Ser
850                 855                 860
His Leu Asp Ser Ala Ile Arg Ser Glu Met Asn Ser Glu Ile Gly Asp
865                 870                 875                 880
Ser Gly Arg Val Ile Gly Val Ser Phe Ser Ile Asn Pro Cys Ser Ser
            885                 890                 895
Ser Phe Thr Val Gly His Gly Gln Glu His Pro Glu Ile Thr Val Lys
```

```
                900             905              910
Phe Gly Ser Asp Leu Asp Gly Asn Val Thr Asn Ser Leu Ser Met Val
        915              920             925
Asn Gly Asp Ser Ala Asp Leu Thr Leu Thr Ser Ile Ser Arg Glu Gln
        930              935             940
His Gln Gly His Ser Met Thr Ser Asn Asn Asn Gly Ser Asn Ser Gly
945             950              955             960
Ser His Val Val Ala Ser Gln Thr Ile Leu Val Ser Thr Gly Asp Asn
            965              970             975
His Asp Gly Pro Arg Lys Leu Ser Gly Asp Tyr Val Cys Ser Asp Val
            980              985             990
Ser Val Arg Gly Ile Gln Glu Ala Val Glu Met Ser Asp Gln Glu Phe
        995              1000            1005
Gly Glu Pro Arg Ser Thr Val Thr Asn Ile Glu Asp Glu Gln Gln
    1010             1015            1020
Ser Gln Ile Val Lys Pro Thr Gln Arg Glu Ala Val Phe Gly Asp
    1025             1030            1035
His Glu Gln Val Glu Gly Ala Glu Ala Val Ser Thr Arg Glu Asn
    1040             1045            1050
Leu Cys Ser Glu Ile Ile Leu His Thr Glu His Ser Ser Ala His
    1055             1060            1065
Val Gly Met Glu Ile Pro Asp Ile Asn Thr Ala Ser Glu Asn Leu
    1070             1075            1080
Val Val Asp Met Thr His Asp Gly Glu Pro Leu Glu Ser Ser Asp
    1085             1090            1095
Ile Leu Ser Ser Ser Asn Gly Asp Glu Ala Ser Ser Asn Gly Leu
    1100             1105            1110
Gln Val Leu Asn Asp Glu Leu Ser Met Glu Ser Glu Val Ser Ser
    1115             1120            1125
Ser Glu Asn Thr Glu Val Ile Glu Ala Pro Asn Ser Met Gly Glu
    1130             1135            1140
Ala Lys Lys Lys Arg Lys Ile Glu Ser Glu Ser Glu Thr Asn Asp
    1145             1150            1155
Asn Pro Glu Ser Ser Ile Gly Phe Ile Arg Ser Pro Cys Glu Gly
    1160             1165            1170
Leu Arg Ser Arg Gly Lys Arg Lys Ala Thr Cys Glu Thr Ser Leu
    1175             1180            1185
Lys His Thr Glu Thr Ser Asp Glu Glu Lys Lys Pro Ile Ala Lys
    1190             1195            1200
Arg Leu Lys Lys Thr Pro Lys Ala Cys Ser Gly Ser Arg Gln Gln
    1205             1210            1215
Glu Val Pro Thr Thr Thr His Pro Asn Arg Cys Tyr Leu Glu Gly
    1220             1225            1230
Cys Lys Met Thr Phe Glu Ser Lys Ala Lys Leu Gln Thr His Lys
    1235             1240            1245
Arg Asn Arg Cys Thr His Glu Gly Cys Gly Lys Lys Phe Arg Ala
    1250             1255            1260
His Lys Tyr Leu Val Leu His Gln Arg Val His Lys Asp Glu Arg
    1265             1270            1275
Pro Phe Glu Cys Ser Trp Lys Gly Cys Ser Met Thr Phe Lys Trp
    1280             1285            1290
Gln Trp Ala Arg Thr Glu His Leu Arg Leu His Thr Gly Glu Arg
    1295             1300            1305
```

```
Pro Tyr Ile Cys Lys Val Asp Gly Cys Gly Leu Ser Phe Arg Phe
    1310                1315                1320

Val Ser Asp Tyr Ser Arg His Arg Arg Lys Thr Met His Tyr Val
1325                1330                1335

Thr

<210> SEQ ID NO 12
<211> LENGTH: 308
<212> TYPE: PRT
<213> ORGANISM: Oryza sativa

<400> SEQUENCE: 12

Met Pro Pro Pro Pro Pro Ser Leu Thr Ala Asn Thr Ala Ser Ser
1               5                   10                  15

Met Gly Asn Ala Glu Ala Val Val Leu Pro Ala Asn Gly Gly Ala
                20                  25                  30

Arg Arg Arg Ala Asp Lys Val Val His Pro Ala Pro Met Pro Asp Arg
            35                  40                  45

Ala Ala Gly Gly Ala Met Glu Arg Glu Gly Gly Val Gly Gly Gly
        50                  55                  60

Gly Glu Val Gly Gly Trp Arg Arg Pro Glu Trp Cys Ser Ala Ala Gly
65                  70                  75                  80

Val Val Ala Gly Val Leu Arg Arg His Pro Ala Ala Ala Phe Gly
                85                  90                  95

Cys Gly Leu Leu Leu Phe Met Ala Val Glu Tyr Thr Ile Pro Met Val
                100                 105                 110

Pro Pro Ala Ala Pro Pro Val Asp Leu Gly Phe Ala Ala Thr Ala Ala
            115                 120                 125

Leu His Ala Gly Ile Ala Ala Arg Pro Trp Leu Asn Ser Leu Leu Ala
            130                 135                 140

Ala Leu Asn Thr Val Phe Val Ala Met Gln Ala Ala Tyr Ile Leu Trp
145                 150                 155                 160

Ala Ile Leu Gly Glu Gly Arg Pro Arg Ala Ala Val Ala Ala Met Met
                165                 170                 175

Val Phe Thr Cys Arg Gly Ala Leu Gly Cys Ala Thr Gln Leu Pro Leu
                180                 185                 190

Pro Ala Glu Phe Leu Gly Ser Gly Met Asp Phe Pro Val Gly Asn Val
            195                 200                 205

Ser Phe Phe Leu Phe Phe Ser Gly His Val Ala Gly Ala Val Ile Ala
            210                 215                 220

Ala Glu Asp Met Arg Arg Ala Gly Arg Arg Gly Met Ala Arg Leu Tyr
225                 230                 235                 240

Asp Ala Leu Asn Leu Leu Gln Gly Val Arg Leu Leu Ala Cys Arg Gly
                245                 250                 255

His Tyr Thr Ile Asp Leu Ala Val Gly Val Gly Ala Gly Leu Leu Phe
            260                 265                 270

Asp Met Leu Ala Gly Arg Tyr Leu Asp Gly Lys Asn Thr Val Asp Gly
        275                 280                 285

Gly Ala Ala Val Ala Pro Gly Ser Arg Cys Cys Ser Cys His Lys Ala
    290                 295                 300

Leu Leu Ser Gln
305

<210> SEQ ID NO 13
```

```
<211> LENGTH: 305
<212> TYPE: PRT
<213> ORGANISM: Solanum lycopersicum

<400> SEQUENCE: 13

Met Asn Ala Glu Thr Leu His Leu Arg Tyr Ser Ser Ser Ser Phe
1               5                   10                  15

Asn Thr Arg Ser His Ser Ser Ile Asn Gly Phe Gln Phe Glu Asn Met
            20                  25                  30

Glu Met Glu Asp Asp Asn Lys Ile Thr Asp Met Lys Lys Arg Pro Pro
                35                  40                  45

Ser Glu Phe Gly Asp Ser Gly Trp Leu Arg Asn Thr Phe Phe Met Arg
    50                  55                  60

Leu Thr Ala Arg Asp Val Phe Gly Val Val Lys Asn His Pro Ile Pro
65                  70                  75                  80

Cys Ile Phe Ala Thr Thr Leu Leu Phe Phe Met Gly Val Glu Tyr Thr
                85                  90                  95

Leu His Met Val Pro Ser Ser Pro Pro Phe Asp Leu Gly Phe Val
                100                 105                 110

Ala Thr Arg Pro Leu His Arg Leu Leu Asp Ser Lys Pro Ala Leu Asn
                115                 120                 125

Thr Val Leu Ala Gly Leu Asn Thr Gly Phe Val Gly Met Gln Met Val
130                 135                 140

Tyr Ile Val Trp Ala Phe Leu Ile Glu Gly Arg Pro Arg Ala Thr Ile
145                 150                 155                 160

Ala Thr Leu Phe Met Phe Thr Cys Arg Gly Ile Leu Gly Tyr Ser Thr
                165                 170                 175

Gln Leu Pro Leu Pro Glu Asp Phe Leu Gly Ser Gly Ala Asp Phe Pro
                180                 185                 190

Val Gly Asn Val Ser Phe Phe Leu Phe Tyr Ser Gly His Val Ala Ala
                195                 200                 205

Ser Val Ile Ala Ser Leu Asp Met Lys Arg Met Gln Arg Trp Lys Leu
                210                 215                 220

Ser Tyr Leu Phe Asp Thr Leu Asn Val Leu Gln Thr Val Arg Leu Leu
225                 230                 235                 240

Ser Thr Arg Gly His Tyr Thr Ile Asp Leu Ala Val Gly Val Gly Ala
                245                 250                 255

Gly Ile Leu Phe Asp Ser Leu Ser Gly Lys Tyr Glu Glu Lys Arg Lys
                260                 265                 270

Lys Glu Leu Leu Ala Gly Ser Pro Asp Gly Ser Thr Asn Gly Ala Phe
                275                 280                 285

His Asn Ser Lys Leu His Glu Asn Gly Glu Tyr Leu Ser Val Ser Ala
                290                 295                 300

Asp
305

<210> SEQ ID NO 14
<211> LENGTH: 267
<212> TYPE: PRT
<213> ORGANISM: Glycine max

<400> SEQUENCE: 14

Met Asn Gly Gly Ala Glu Ala Ser Leu Asn His Arg Arg Lys His Gln
1               5                   10                  15

Thr Ala Pro Ala Asp Gly Ala Lys Gly Val Lys Val Ala Asn Gly Ala
            20                  25                  30
```

Met Gly Lys Pro Ser Ser Ser Lys His Ser Cys Gly Ala Ser Phe Met
                35                  40                  45

Lys Trp Thr Val Ala Asp Ala Val His Val Val Thr His His Trp Ile
    50                  55                  60

Pro Cys Leu Phe Ala Leu Gly Leu Leu Phe Phe Met Ala Val Glu Tyr
65                  70                  75                  80

Thr Leu Leu Met Val Pro Pro Ser Ser Pro Pro Phe Asp Leu Gly Phe
                85                  90                  95

Ile Ala Thr Arg Ser Leu His Ala Leu Leu Glu Ser Ser Pro Asn Leu
                100                 105                 110

Asn Thr Leu Phe Ala Gly Leu Asn Thr Val Phe Val Gly Met Gln Thr
                115                 120                 125

Ser Tyr Ile Leu Trp Thr Trp Leu Ile Glu Gly Arg Pro Arg Ala Thr
                130                 135                 140

Ile Ser Ala Leu Phe Met Phe Thr Cys Arg Gly Ile Leu Gly Tyr Ser
145                 150                 155                 160

Thr Gln Leu Pro Leu Pro Gln Gly Phe Leu Gly Ser Gly Val Asp Phe
                165                 170                 175

Pro Val Gly Asn Val Ser Phe Phe Leu Phe Phe Ser Gly His Val Ala
                180                 185                 190

Gly Ser Val Ile Ala Ser Leu Asp Met Arg Arg Met Gln Arg Trp Glu
                195                 200                 205

Leu Ala Trp Thr Phe Asp Val Leu Asn Val Leu Gln Ala Val Arg Leu
                210                 215                 220

Leu Gly Thr Arg Gly His Tyr Thr Ile Asp Leu Ala Val Gly Val Gly
225                 230                 235                 240

Ala Gly Ile Leu Phe Asp Ser Leu Ala Gly Lys Tyr Glu Asp Ser Lys
                245                 250                 255

Arg Asn Gly Ala Leu Lys His Asn Leu Ile Ala
                260                 265

<210> SEQ ID NO 15
<211> LENGTH: 298
<212> TYPE: PRT
<213> ORGANISM: Arabidopsis thaliana

<400> SEQUENCE: 15

Met Ser Ala Ala Ala Glu Thr Asp Val Ser Leu Arg Arg Arg Ser
1               5                   10                  15

Asn Ser Leu Asn Gly Asn His Thr Asn Gly Val Ala Ile Asp Gly Thr
                20                  25                  30

Leu Asp Asn Asn Arg Arg Val Gly Asp Thr Asn Thr His Met Asp
                35                  40                  45

Ile Ser Ala Lys Lys Thr Asp Asn Gly Tyr Ala Asn Gly Val Gly Gly
50                  55                  60

Gly Gly Trp Arg Ser Lys Ala Ser Phe Thr Thr Trp Thr Ala Arg Asp
65                  70                  75                  80

Ile Val Tyr Val Val Arg Tyr His Trp Pro Cys Met Phe Ala Ala Gly
                85                  90                  95

Leu Leu Phe Phe Met Gly Val Glu Tyr Thr Leu Gln Met Pro Ala Arg
                100                 105                 110

Ser Glu Pro Phe Asp Leu Gly Phe Val Val Thr Arg Ser Leu Asn Arg
                115                 120                 125

Val Leu Ala Ser Ser Pro Asp Leu Asn Thr Val Leu Ala Ala Leu Asn

```
                    130                 135                 140
Thr Val Phe Val Gly Met Gln Thr Thr Tyr Ile Val Trp Thr Trp Leu
145                 150                 155                 160

Val Glu Gly Arg Ala Arg Ala Thr Ile Ala Ala Leu Phe Met Phe Thr
                165                 170                 175

Cys Arg Gly Ile Leu Gly Tyr Ser Thr Gln Leu Pro Leu Pro Gln Asp
                180                 185                 190

Phe Leu Gly Ser Gly Val Asp Phe Pro Val Gly Asn Val Ser Phe Phe
                195                 200                 205

Leu Phe Phe Ser Gly His Val Ala Gly Ser Met Ala Ser Leu Asp Met
                210                 215                 220

Arg Arg Met Gln Arg Leu Arg Leu Ala Met Val Phe Asp Ile Leu Asn
225                 230                 235                 240

Val Leu Gln Ser Ile Arg Leu Leu Gly Thr Arg Gly His Tyr Thr Ile
                245                 250                 255

Asp Leu Ala Val Gly Val Gly Ala Gly Ile Leu Phe Asp Ser Leu Ala
                260                 265                 270

Gly Lys Tyr Glu Glu Met Met Ser Lys Arg His Leu Gly Thr Gly Phe
                275                 280                 285

Ser Leu Ile Ser Lys Asp Ser Leu Val Asn
                290                 295

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 16
atccctggtg tcacatctcc                                              20

<210> SEQ ID NO 17
<211> LENGTH: 19
<212> TYPE: DNA
<213> ORGANISM: Artificial Sequence
<220> FEATURE:
<223> OTHER INFORMATION: synthetic oligonucleotide primer

<400> SEQUENCE: 17
gctcatggtc ctcaacgtg                                               19

<210> SEQ ID NO 18
<211> LENGTH: 22
<212> TYPE: DNA
<213> ORGANISM: Artificial Sequence
<220> FEATURE:
<223> OTHER INFORMATION: synthetic oligonucleotide primer

<400> SEQUENCE: 18
taagctcatg gtcctcaacg ta                                           22

<210> SEQ ID NO 19
<211> LENGTH: 19
<212> TYPE: DNA
<213> ORGANISM: Artificial Sequence
<220> FEATURE:
<223> OTHER INFORMATION: synthetic oligonucleotide primer

<400> SEQUENCE: 19
cctggtgaat tgttgtga                                                19
```

<210> SEQ ID NO 20
<211> LENGTH: 18
<212> TYPE: DNA
<213> ORGANISM: Artificial Sequence
<220> FEATURE:
<223> OTHER INFORMATION: synthetic oligonucleotide primer

<400> SEQUENCE: 20
ggacagcatg ggaagata                                             18

<210> SEQ ID NO 21
<211> LENGTH: 16
<212> TYPE: DNA
<213> ORGANISM: Artificial Sequence
<220> FEATURE:
<223> OTHER INFORMATION: synthetic oligonucleotide primer

<400> SEQUENCE: 21
gctatcaaca agcttc                                               16

<210> SEQ ID NO 22
<211> LENGTH: 16
<212> TYPE: DNA
<213> ORGANISM: Artificial Sequence
<220> FEATURE:
<223> OTHER INFORMATION: synthetic oligonucleotide primer

<400> SEQUENCE: 22
gcaccatgag ctacta                                               16

<210> SEQ ID NO 23
<211> LENGTH: 23
<212> TYPE: DNA
<213> ORGANISM: Artificial Sequence
<220> FEATURE:
<223> OTHER INFORMATION: synthetic oligonucleotide primer

<400> SEQUENCE: 23
gtgagacaca ccatcaccag aat                                       23

<210> SEQ ID NO 24
<211> LENGTH: 21
<212> TYPE: DNA
<213> ORGANISM: Artificial Sequence
<220> FEATURE:
<223> OTHER INFORMATION: synthetic oligonucleotide primer

<400> SEQUENCE: 24
tgtcgccatc caagctgttc t                                         21

<210> SEQ ID NO 25
<211> LENGTH: 19
<212> TYPE: DNA
<213> ORGANISM: Artificial Sequence
<220> FEATURE:
<223> OTHER INFORMATION: synthetic oligonucleotide primer

<400> SEQUENCE: 25
agttaagagg actgtctgg                                            19

<210> SEQ ID NO 26
<211> LENGTH: 18
<212> TYPE: DNA
<213> ORGANISM: Artificial Sequence
<220> FEATURE:

```
<223> OTHER INFORMATION: synthetic oligonucleotide primer

<400> SEQUENCE: 26
tcctgaacca tatcctct                                                     18
```

EARLY FLOWERING PLANTS

CROSS-REFERENCE TO RELATED APPLICATIONS

This application claims the benefit of U.S. Patent Application Ser. No. 62/547,668, filed on Aug. 18, 2017. The disclosure of the prior application is considered part of (and is incorporated by reference in) the disclosure of this application.

STATEMENT REGARDING FEDERAL FUNDING

This invention was made with government support under 2014-67009-22305 and NA/013080 awarded by the National Institute of Food and Agriculture, USDA. The government has certain rights in the invention.

BACKGROUND

1. Technical Field

This document relates to materials and methods for generating early flowering oilseed (e.g., pennycress) plants. For example, this document provides oilseed plants (e.g., modified oilseed plants) having one or more modifications in a polypeptide involved in early flowering (e.g., early flowering six (ELF6)), as well as materials and methods for making and using early flowering oilseed plants.

2. Background Information

Oilseed crops are sources of oils and seed meal having a multitude of uses. Winter annual varieties of pennycress (*Thlaspi arvense* L.) have been developed into a new crop species that can be grown on the fallow land available between the harvest of corn and the sowing of soybeans the following year (Phippen et al., 2012 Crop Science, 52:2767-2773). There are over eighty million acres undergoing the corn/soybean rotation that could be used for double cropping pennycress.

SUMMARY

This document provides materials and methods for generating early flowering oilseed (e.g., pennycress) plants. For example, this document provides oilseed that develop flowers and/or seed pods earlier than corresponding wild type oilseed plants. In some cases, oilseed plants (e.g., modified oilseed plants) having one or more modifications in a polypeptide involved in early flowering (e.g., ELF6) can have early development of flowers and/or seed pods. For example, the early flowering oilseed plants described herein can include one or more modifications in an ELF6 gene (e.g., in the coding sequence of an ELF6 gene) such that the modified ELF6 gene encodes a modified ELF6 polypeptide. This document also provides materials and methods for making and/or using the early flowering oilseed (e.g., pennycress) plants described herein.

As demonstrated herein, loss-of-function modifications in the coding sequence of the pennycress ELF6 gene (e.g., a single base-pair substitution of a cytosine (C) to thymine (T) at residue 952 in SEQ ID NO:1) resulted in early flowering and early seed pod production as compared to corresponding wild type pennycress plants. The early flowering plants maintain cold hardiness and are able to recover following a hard freeze.

The early flowering pennycress plants described herein can produce oilseeds in a shortened growing period, and can therefore be double cropped (e.g., grown in the time interval between the harvest of a first crop (e.g., corn) and the establishment of a second crop (e.g., soybeans)) without delaying establishment of the second crop. The early flowering pennycress plants described herein can provide a new source of oilseeds that can be used for the production of, for example, biofuels, bioproducts, animal feed supplements, and/or edible oil.

In general, one aspect of this document features an oilseed plant that flowers early as compared to a corresponding wild type oilseed plant, and where the oilseed plant includes a modification in an ELF6 gene. The oilseed plant can be a pennycress plant. The oilseed plant can flower about 10 days to about 25 days early (e.g., about 24 days early). The modification can include a substitution. The substitution can be a single base-pair substitution of the cytosine at residue 952. The substitution can be a cytosine to guanine substitution. The modified ELF6 gene can include the sequence set forth in SEQ ID NO:3. The modified ELF6 gene can encode a modified ELF6 polypeptide. The modified ELF6 polypeptide can include the sequence set forth in SEQ ID NO:4. In some cases, the oilseed plant also can have a low level of linoleic acid and an elevated level of oleic acid. The oilseed plant can include a modification in a ROD1 gene. The modified ROD1 gene can include a single base-pair substitution of the cytosine at residue 1918. The substitution can be a guanine to adenine substitution. The modified ROD1 gene can include the sequence set forth in SEQ ID NO:7. The modified ROD1 gene can encode a modified ROD1 polypeptide. The modified ROD1 polypeptide can include the sequence set forth in SEQ ID NO:8.

In another aspect, this document features a seed produced by an oilseed plant that flowers early as compared to a corresponding wild type oilseed plant, and where the oilseed plant includes a modification in an ELF6 gene, and, optionally, in the ROD1 gene.

In another aspect, this document features a method for generating an oilseed plant that flowers early as compared to a corresponding wild type oilseed plant. The method includes, or consists essentially of, modifying an ELF6 gene in the oilseed plant genome, where the modified ELF6 gene encodes a modified ELF6 polypeptide, and where the modified ELF6 polypeptide can be effective to cause early flowering in the oilseed plant. The oilseed plant can be a pennycress plant. The modifying can include site-specific editing. The modification can include a substitution. The substitution can include a single base-pair substitution of the cytosine at residue 952. The substitution can include a cytosine to guanine substitution. The modified ELF6 gene can include the sequence set forth in SEQ ID NO:3. The modified ELF6 polypeptide can include the sequence set forth in SEQ ID NO:4. In some cases, the method also can include modifying a ROD1 gene in the oilseed plant genome, where the modified ROD1 gene encodes a modified ROD1 polypeptide, where the modified ROD1 polypeptide can be effective to cause a low level of linoleic acid and an elevated level of oleic acid in the oilseed plant. The modified ROD1 gene can include a single base-pair substitution of the cytosine at residue 1918. The substitution can be a guanine to adenine substitution. The modified ROD1 gene can include the sequence set forth in SEQ ID NO:7. The modified ROD1 polypeptide can include the sequence set forth in SEQ ID NO:8.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 4A-4C show WT and modified ELF6 sequences. FIG. 4A contains a nucleic acid sequence of residues 758 to 1096 of SEQ ID NO:1 showing the cytosine at residue 952 of SEQ ID NO:1 (underlined) and indicating the position of primers for amplifying residues 758 to 1096 of SEQ ID NO:1. FIG. 4B contains a sequencing read showing residues 944 to 960 of SEQ ID NO:1, and showing the cytosine at residue 952 of SEQ ID NO:1. FIG. 4C contains a polypeptide sequence alignments comparing a wild type ELF6 polypeptide from *Arabidopsis thaliana* (At_ELF6; SEQ ID NO:11), a wild type ELF6 polypeptide from *Thlaspi arvense* (pennycress; Ta_ELF6; SEQ ID NO:2), and a modified ELF6 polypeptide from *Thlaspi arvense* (pennycress; Ta_ELF6_mutant; SEQ ID NO:4). The histidine (H) residue at position 318 in *Arabidopsis* is conserved in pennycress, and is also conserved in, for example, rice, tomato, and soybean.

FIG. 5E is a gene model for an early flowering pennycress plant having a modified ELF6 gene encoding a modified ELF6 polypeptide having a H to Y substitution. The bar across the top of the gene model represents 200 bp.

FIGS. 6A-6C show an analysis of oil content in pennycress plants. A) Near infrared (NIR) spectroscopy-derived fatty acid profiles showing oil content (e.g., fatty acid profiles: 16:00=palmitic acid; 18:00=stearic acid; 18:01=oleic acid; 18:02=linoleic acid; 18:03=linolenic acid; 20:01=eicosenoic acid; and 22:01=erucic acid) in wild type (MN 106) and mutant pennycress (PC) plants having a modification in the FAE1-1, FAE1-2, or ROD1-1 gene. B) A gene model for a pennycress plant having a modified ROD1-1 gene encoding a modified ROD1-1 polypeptide having a G to A substitution. C) A sequence alignment of ROD1 polypeptides from *Oryza sativa* (Os; SEQ ID NO:12); *Solanum lycopersicum* (Sl; SEQ ID NO:13), *Glycine max* (Gm; SEQ ID NO:14), *Arabidopsis thaliana* (At; SEQ ID NO:15), wild type MN 106 pennycress (Ta; SEQ ID NO:6), and a ROD1 mutant having an altered fatty acid (Ta_ROD1_mutant; SEQ ID NO:8).

DETAILED DESCRIPTION

Figure 1:
FIG. 1 contains images of pennycress plants in the field on March 22. On the left is a wild type (MN 106) pennycress plant. On the right is an A7 25 pennycress plant showing early flowering. Wild type control plants shown on the left did not flower until after April 15.

This document relates to early flowering oilseed (e.g., pennycress) plants. In some cases, this document provides oilseed plants (e.g., modified oilseed plants) having one or more modifications in one or more polypeptides involved in early flowering (e.g., ELF6) as compared to corresponding wild type pennycress plants. For example, an early flowering oilseed plant can have one or more modifications in an ELF6 gene (e.g., in an ELF6 coding sequence) such that the modified ELF6 gene encodes a modified ELF6 polypeptide that is effective to cause early flower development. This document also relates to methods and materials for making and using early flowering oilseed plants. In some cases, site-specific gene editing can be used to modify an ELF6 gene (e.g., an ELF6 coding sequence). For example, site-specific editing can be used to modify the ELF6 gene in an oilseed plant genome to alter (e.g., reduce) ELF6 polypeptide expression and/or alter (e.g., reduce) ELF6 polypeptide function. As described herein, gene editing techniques (e.g., CRISPR-Cas systems) can be used to produce an oilseed plant having a loss-of-function modification in an ELF6 gene. For example, one or more modifications can be made to an ELF6 gene in a plant, which can be effective to cause reduced expression and/or reduced activity of an ELF6 polypeptide and thereby cause early flowering in the plant.

The early flowering oilseed plants described herein can be derived from any appropriate species of oilseed plant. An oilseed plant can be a monocotyledonous oilseed plant, or an oilseed plant can be a dicotyledonous oilseed plant. An oilseed plant can be a member of the family Brassicaceae (e.g., the mustard family). For example, an oilseed plant can be a member of the genus *Brassica*. Examples of oilseed plants include, without limitation, pennycress, rapeseed, soybean, sunflower, canola, flax, camelina, carinata, crambe, and lepidium plants. In some cases, an early flowering oilseed plant described herein can be a pennycress plant.

The term "early flowering" as used herein refers to any plant that flowers earlier than a control plant flowers. The term "control plant" as used herein refers to a comparable oilseed plant having a wild type ELF6 gene and expressing a wild type ELF6 polypeptide. For example, a wild type pennycress plant typically produces flowers in the early spring after sowing in the fall. In some cases, an early flowering pennycress plant described herein can produce flowers by about 10 days to about 25 days (e.g., about 12 days to about 25 days, about 15 days to about 25 days, about 17 days to about 25 days, about 20 days to about 25 days, about 10 days to about 22 days, about 10 days to about 20 days, about 10 days to about 18 days, about 10 days to about 15 days, about 10 days to about 12 days, about 12 days to about 20 days, or about 15 days to about 18 days) earlier than a corresponding control plant. For example, an early flowering pennycress plant described herein (e.g., A7 25) can flower about 24 days earlier than a corresponding control plant.

In some cases, the early flowering oilseed plants described herein can develop seed pods early. The term "early seed pod development" as used herein refers to any plant that develops seed pods earlier than a control plant develops seed pods. The term "control plant" as used herein refers to a comparable oilseed plant having a wild type ELF6 gene and expressing a wild type ELF6 polypeptide. For example, an early flowering pennycress plant described herein (e.g., A7 25) can produce seed pods about 11 days earlier than a corresponding control plant.

In some cases, the early flowering oilseed plants described herein require vernalization (e.g., prolonged exposure to 4° C.) in order to initiate flowering. Vernalization temperatures can include, for example, temperatures between about 40° F. and about 50° F. (e.g., between about 5° C. and about 10° C.).

In some cases, the early flowering oilseed plants described herein also can have increased tolerance (e.g., an increased ability to survive and recover from exposure to) to cold temperatures. In some cases, cold temperatures can include a hard freeze (e.g., temperatures at or below 19° F. (−7° C.) during the growing season). For example, an early flowering pennycress plant described herein (e.g., A7 25) can recover about 5 days after a hard freeze.

The early flowering oilseed plants described herein can include one or more modifications in a gene that encodes a polypeptide involved in flower development. In some cases, the one or more modifications in a gene that encodes a polypeptide involved in flower development can be in the coding sequence. Polypeptides involved in flower development include, without limitation, ELF6, FLC, and FRI. For example, an early flowering oilseed plant described herein can include one or more modification in the ELF6 gene (e.g., coding sequence). A representative WT pennycress ELF6 coding sequence is as follows (SEQ ID NO:1), with lower case letters indicating introns.

ATGGGTGATGTTGAAATTCCCAATTGGCTAAAAGCCTTGCCTTTGGCAC

CTGTCTTTAGACCTACGGACACCGAATTCGCAGATCCTATCGCGTATAT

ATCGAAAATCGAGAAAGAGGCCAGTGCTTTTGGGATCTGCAAGATCATT

CCTCCTTTACCCAAGCCGTCGAAAAAGTATGTTTTCTACAACTTGAACA

AGTCTCTTTTGAGGTGTCCTGAATTGGCTTCGGATGTAGACATTTCGAA

AGTGTGTCAAGAGGATAGAGCTGTGTTCACCACTAGGCAGCAAGAGTTA

GGGCAGGCTGTAAAACGAAAGAAAGGAGGAGAGAGCAGTAAGAGCAATT

CTCAAAGGAGTGGCGTTAAGCAGGTGTGGCAAAGTGGAGGCGTGTACAC

GTTGGAGCAGTTCGAATCTAAGTCAAAAACTTTCTACAAAAGCCAGTTA

GGAACCACAAAAGAAGTGCCACCGGTTGTGGTTGAGGCATTGTTCTGGA

AAGCAGCTTTAGAGAAGCCTATATACATAGAGTATGCAAATGATGTGCC

TGGCTCGGCTTTCGGTGAACCAGAGGGTCATTTCAGGCATTTTCGGCAG

AGAAAGAGGAGAGGGAGAGGATTTTATCAGAGGAAGGCAGAGGTCAGTG

AAGACAGCGGAGTAGAAAACGGGACGAATAGTCAAGAACCAACCTGCAA

GAATGGTGAGAAAACATTGCCTGAGGTAGCAAAGGCATCTCTTGCTTCT

CCGAGTTTATTATCTCAGGATCCGTCCAAGCAGAAGAACATGGATATTG

TTGATGAAATGGAAGGTACTGCAGGCTGGAAGCTCTCCAACAGTTCATG

GAACCTTCAGATGATTGCACGTTCACCTGGATCTGTTACACGCTTCATG

CCAGATGACATCCCTGGTGTCACATCTCCCATGGTTTATATCGGTATGT

TGTTCAGCTGGTTTGCCTGGCACGTTGAGGACCATGAGCTTCACAGTAT

GAATTACCTTCACACTGGCTCGCCAAAGACGTGGTACGCTGTCCCTGGT

GATTATGCATTTGACTTTGAAGAGGTTATCCGCAAAAATTCGTATGGCA

GAAACATTGATCAACTGGgtacgttctttctgaaaagtactgctaaata tgatatactgtttctgtttatatagaaatgtttcgttggtgtaatacat catacatgtgagaaatgagatttcctagaatgattaccgcatccatatt tttctttactagcacctttttttttttgctttgtaagtgaaatgtggctg acattgactatgatatgacgagagtttgtactcttgggaaattgcgtta ggacttattgctttaaggttattatgatagatatgagacgttgcaacac ttcttatgaaatgcattgtccttctgtttctcattgactcttagctgtt ctttgtcactttcagCTGCTCTCACCCAACTAGGCGAAAAGACAACTCT TGTATCACCTGAGATGATAATTGCATCTGACATTCCCTGCTGTAGgtag gccttttaattttatttgaactttcacttctgttatgtggagatgtgag gcagtttgtgttttcttataactacgccaagctctgctatatctatttt tgttttcccacgtagGTTGGTACAGAATCCTGGTGAATTTGTTGTGACT TTTCCGAGGTCTTATCATGTAGGATTCAGCCACGgtaaaaatgcttttt ttcttcaaacattcttaagtctttgtgactttactttggtcgtcccatt ttgcactcttcaaagtgtgtgagaaaatgtgaaaattcaaaattcaaaa ttgagtaaagctttggagaaaaatgagtgtttttacgacagagcataagg tgaggattgatcttctaattaggagaatgaagaaccaaatttctattaa gtagtagttatataagttgcatagtaaaagcggatagtttggcttcgat taggaatacaaattgcaatatttttttcagaatccttaactaagcagaa ttaatttaacgttttaaagGTTTTAACTGTGGGGAAGCCGCTAATTTTG

GAACTCCACAATGGCTCAACGTAGCTAAGGAAGCTGCTGTGCGACGGGC

AGCCATGAATTATCTTCCCATGCTGTCCCATCAGCAGCTGCTATATCTC

TTGACCATGTCCTTTGTTTCAAGGCAAATTTCCATGGCCTCTTTgtaca tagaaccctttctgctgaacctgttaatcctcatattcttgtaaata ttaaaattttcagAGTGCCACGATCATTACTACCAGGTGGTCGTAGCTC

CCGACTGAGAGATCGTCAGAGAGAAGAAAGGGAGTTCCTTGTGAAAAAA

GCTTTTGTAGAAGATATACTGAACGAAAACAAGAATTTATCTGTTCTTC

```
ATCGAGAACCGGGATTTCGTTTGGTGATGTGGGACCCTGATTTACTCCC
GCGTCATAGTGTACATGGTCTTGTAACTGTTGGGGGTGCTGCTGTTTCA
TCTCCAGCAGAGGGAAAAAATGAACTTGAGGAGAAGAATAAAGAGAAGA
CTACTCTTTTAGAGGAATTGAGTTTGTTCATGGAGAAGCTGAAAGATGT
ATACTACGACGATGATGATGGTCTGCTTAATGATTTCCAGGTTGATTCT
GGAACCTTGGCATGTGTGGCGTGTGGCGTTCTTGGCTTCCCCTTTATGT
CTGTGGTACAGCCTTCTGAAAATGCATTAAATGATCTTTCAGAGAGACG
AGGAGAGATAGgtaacagaccctcattttttaaccaaactatgaacta
caccatcttcgtttgaagcctgttaattgtgcttctatctattctacag
ATGGTCAGGAAATTACGGCACTGTTGTCAGAAAAGTCTGACTGTGAATG
GAACATGTCCTCCAGGTATATAAGACCTCGCATTTTCTGCCTCGAACAC
ACTATTGAGCTCCAGAGACTGCTGGAGTCACGAGGTGGACTGAAGTTCC
TTGTAATTTGCCATAAAGgtaagtacgcgtcatttgctattaaattcga
tgccaaagagaatattttgatcattctgcttttaacttttttttggaatt
gttgcagACTTTCAAAAATTTAAGGCATATGCGGCTATAGTGGCAGAGG
AAGTTAAAGTCCCTTTCAGCTATGATGATATCCTGTTAGAGAGTGCATC
TAAAGAAGAGTTGAGTCTGATTGATCTTGCAATTGAAGATGAAGAAAAC
AACGAACATGGCGTAGACTGGACCTCAAAACTTGGTATCAATTTACGGT
ACTGTGTTAAAGTGAGGAAAAATTCCCCTTCTACGAAAATTCAGCATGC
ACTGTCGCTAGGTGGCTTGTTCTCCGATACAAACCACATGCTAGATATG
TCAACTATCAAATGGCTGCAGAGAAAATCACGCTCAAAAGCCAAACCCA
GTTGTACCTCAAGCTTCACACCTCGTGAACATCTTGAAGTAAAAGTAGA
CAGAAAATTAGGGGAGAAGGAAAAAGTTGAATCCCAAGCCGGAAGAAAG
GAAGAAAAGATCATCCAGTACTCGAGAAAGAAAAAGTTGAAGCCCAAGC
CTTCTGAAGAACGAAGTCAGGAACTAACTATCTCAGCTAAATCAGAAGA
TTTTGAAAACACATGCAACACACTTGCCAAAAGGTCACATCATCATGGG
GCAATGCATTCTGATATGAACAATGAAATTGGAGATTTTGGGAGGAATG
GGGTATCCTTTTCAGAAAATCATTGTAGCTCACCTTTCACTGGGGCACG
CGGACAAGAACATCCCAAGATCATTATCAAGTTTGGCTCAGCATTACAT
GGGAATATTACAAGCAGTTCTAGTTTGGTGAATGGAATCTCTGCTGACC
TAACTTCCGTAACCAGAGAGCACCAAGGACACTCTATGACCAGCAATAA
TAATGGGTCGAACTCAAGTAATCATGATGGCCCAATAAAGCTGTCTGGT
GAGCATGTCAGTGACGTGTCTGTACGTGATGTTGATGAAGCGGTTGAAA
TGAGCGACCAAGAGTTCGAAGAACTGAGGTCTACCGTCACTAACATTGA
GGAGGAACAGCAATCAGAGATGGTGAGACCAACCGCACTTCAGGTGGAG
GGAGAGGAATCTATGTGTACGAGAGAAATCTTGAGCTCTGAAGATATTA
TGCACACTGAGCAGCAGCAAGAGCAAACTCAACTGGGTTTAGAAGTTCC
TGAAACTGACATTGCCAGTGAGAACATAGTTGTGGACATGATCCATGAT
GATGAACCTCTGGCAACTAGGGATATATTAAGTTCAAGCAACGGTGATC
AAGCTTCTTCAAATGGCTTGCAAGCTCTAGATAATGAACTTAGCATGGA
GAGCGAAGTTGCAAGCTCAGAAAACACCGAGGTTATAGAGGCGTCGCCC
AATTCTATTATGCGAGAAGCAAATAAGAAGCGGAGAATAGAATCAGAGT
CTGAGACAAATGATAATCCAGATGGTAGCATTGGTTTCATAAGGAGTCC
TTGTGAAGGGTTGAGGTCAAGGGGTAGGAGGAGAGTGACGCGTGAAGCT
TCAGTCAGTCTCACTGAAACGAGCGATGAAGAGAAGAAACCCGCTGCGA
AAAGGTTCAAGAAAACTCCAAAGACTCGCTCGGGGAGTCATCACCAAGA
AGACTCCACGACAAGTCACCACAACCGTTGTAACCTAGAGGGATGCAAG
ATGACTTTCAAGAGTAAAGCAGAGTTACAAGCTCACCAAAGAAACCGCT
GCGCACATGAAGGGTGTGGAAAAAAATTCAGGGCTCACAAATATCTGGT
GCTTCATCAACGTGTTCATAACGATGATAGACCTTTTGTGTGCTCTTGG
AAAGGATGTTCCATGACTTTCAAATGGCCATGGGCGAGGACCGAGCATT
TGCGTCTGCACACGGGAGAGCGACCATACAAATGCAAGGTCGATGGATG
TGGAATGTCGTTTAGGTTTGTGTCGGATTACAGCCGCCATAGACGGAAA
AAGGGGCATTATGTGACATAG
```

In some cases, a WT pennycress ELF6 gene (e.g., coding sequence) can have a sequence that deviates from the sequence set forth above (SEQ ID NO:1), sometimes referred to as a variant sequence, provided the variant sequence encodes a WT pennycress ELF6 polypeptide. A representative WT pennycress ELF6 polypeptide is as follows (SEQ ID NO:2).

```
MGDVEIPNWLKALPLAPVFRPTDTEFADPIAYISKIEKEASAFGICKII
PPLPKPSKKYVFYNLNKSLLRCPELASDVDISKVCQEDRAVFTTRQQEL
GQAVKRKKGGESSKSNSQRSGVKQVWQSGGVYTLEQFESKSKTFYKSQL
GTTKEVPPVVVEALFWKAALEKPIYIEYANDVPGSAFGEPEGHFRHFRQ
RKRRGRGFYQRKAEVSEDSGVENGTNSQEPTCKNGEKTLPEVAKASLAS
PSLLSQDPSKQKNMDIVDEMEGTAGWKLSNSSWNLQMIARSPGSVTRFM
PDDIPGVTSPMVYIGMLFSWFAWHVEDHELHSMNYLHTGSPKTWYAVPG
DYAFDFEEVIRKNSYGRNIDQLAALTQLGEKTTLVSPEMIIASDIPCCR
LVQNPGEFVVTFPRSYHVGFSHGFNCGEAANFGTPQWLNVAKEAAVRRA
AMNYLPMLSHQQLLYLLTMSFVSRQISMASLVPRSLLPGGRSSRLRDRQ
REEREFLVKKAFVEDILNENKNLSVLHREPGFRLVMWDPDLLPRHSVHG
LVTVGGAAVSSPAEGKNELEEKNKEKTTLLEELSLFMEKLKDVYYDDDD
GLLNDFQVDSGTLACVACGVLGFPFMSVVQPSENALNDLSERRGEIDGQ
EITALLSEKSDCEWNMSSRYIRPRIFCLEHTIELQRLLESRGGLKFLVI
CHKDFQKFKAYAAIVAEEVKVPFSYDDILLESASKEELSLIDLAIEDEE
NNEHGVDWTSKLGINLRYCVKVRKNSPSTKIQHALSLGGLFSDTNHMLD
MSTIKWLQRKSRSKAKPSCTSSFTPREHLEVKVDRKLGEKEKVESQAGR
KEEKIIQYSRKKKLKPKPSEERSQELTISAKSEDFENTCNTLAKRSHHH
GAMHSDMNNEIGDFGRNGVSFSENHCSSPFTGARGQEHPKIIIKFGSAL
HGNITSSSSLVNGISADLTSVTREHQGHSMTSNNNGSNSSNHDGPIKLS
GEHVSDVSVRDVDEAVEMSDQEFEELRSTVTNIEEEQQSEMVRPTALQV
```

```
EGEESMCTREILSSEDIMHTEQQQEQTQLGLEVPETDIASENIVVDMIH

DDEPLATRDILSSSNGDQASSNGLQALDNELSMESEVASSENTEVIEAS

PNSIMREANKKRRIESESETNDNPDGSIGFIRSPCEGLRSRGRRRVTRE

ASVSLTETSDEEKKPAAKRFKKTPKTRSGSHHQEDSTTSHHNRCNLEGC

KMTFKSKAELQAHQRNRCAHEGCGKKFRAHKYLVLHQRVHNDDRPFVCS

WKGCSMTFKWPWARTEHLRLHTGERPYKCKVDGCGMSFRFVSDYSRHRR

KKGHYVT
```

In some cases, a WT pennycress ELF6 polypeptide can have a sequence that deviates from the polypeptide sequence set forth above (SEQ ID NO:2), sometimes referred to as a variant sequence, provided the polypeptide maintains its WT function. For example, as ELF6 polypeptide can have at least 80 (e.g., at least 85, at least 90, at least 95, at least 98, or at least 99) percent sequence identity to SEQ ID NO:2. An ELF6 polypeptide can have one or more (e.g., 2, 3, 4, 5, 6, 7, 8, 9, or 10) amino acid modifications (e.g., substitutions) relative to SEQ ID NO:2.

In some cases, early flowering oilseed plants as described herein can include a one or more modifications in an ELF6 gene (e.g., in an ELF6 coding sequence). Examples of genetic modifications include, without limitation, deletions, insertions, substitutions, frameshifts, duplications, and rearrangements. In some cases, early flowering oilseed plants described herein can include a substitution (e.g., a single base-pair substitution) relative to the WT pennycress ELF6 coding sequence (e.g., SEQ ID NO:1). For example, a modified ELF6 coding sequence can include a substitution of the cytosine (C) at residue 952 in a WT pennycress ELF6 coding sequence (e.g., SEQ ID NO:1). The C at residue 952 can be substituted with any appropriate nucleotide (e.g., adenine (A), guanine (G), and thymine (T)). For example, a modified ELF6 coding sequence can include a single T substituted for the C at nucleotide residue 952 in a WT pennycress ELF6 coding sequence (see, e.g., FIG. 4A). A representative modified pennycress ELF6 coding sequence having a single base-pair substitution at nucleotide residue 952 is as follows (SEQ ID NO:3), with the bold, italic T indicating the substitution, and the lower case letters indicating introns.

```
ATGGGTGATGTTGAAATTCCCAATTGGCTAAAAGCCTTGCCTTTGGCAC

CTGTCTTTAGACCTACGGACACCGAATTCGCAGATCCTATCGCGTATAT

ATCGAAAATCGAGAAAGAGGCCAGTGCTTTTGGGATCTGCAAGATCATT

CCTCCTTTACCCAAGCCGTCGAAAAAGTATGTTTTCTACAACTTGAACA

AGTCTCTTTTGAGGTGTCCTGAATTGGCTTCGGATGTAGACATTTCGAA

AGTGTGTCAAGAGGATAGAGCTGTGTTCACCACTAGGCAGCAAGAGTTA

GGGCAGGCTGTAAAACGAAAGAAAGGAGGAGAGAGCAGTAAGAGCAATT

CTCAAAGGAGTGGCGTTAAGCAGGTGTGGCAAAGTGGAGGCGTGTACAC

GTTGGAGCAGTTCGAATCTAAGTCAAAAACTTTCTACAAAAGCCAGTTA

GGAACCACAAAAGAAGTGCCACCGGTTGTGGTTGAGGCATTGTTCTGGA

AAGCAGCTTTAGAGAAGCCTATATACATAGAGTATGCAAATGATGTGCC

TGGCTCGGCTTTCGGTGAACCAGAGGGTCATTTCAGGCATTTTCGGCAG

AGAAAGAGGAGAGGGAGAGGATTTTATCAGAGGAAGGCAGAGGTCAGTG

AAGACAGCGGAGTAGAAAACGGGACGAATAGTCAAGAACCAACCTGCAA

GAATGGTGAGAAAACATTGCCTGAGGTAGCAAAGGCATCTCTTGCTTCT

CCGAGTTTATTATCTCAGGATCCGTCCAAGCAGAAGAACATGGATATTG

TTGATGAAATGGAAGGTACTGCAGGCTGGAAGCTCTCCAACAGTTCATG

GAACCTTCAGATGATTGCACGTTCACCTGGATCTGTTACACGCTTCATG

CCAGATGACATCCCTGGTGTCACATCTCCCATGGTTTATATCGGTATGT

TGTTCAGCTGGTTTGCCTGGTACGTTGAGGACCATGAGCTTCACAGTAT

GAATTACCTTCACACTGGCTCGCCAAAGACGTGGTACGCTGTCCCTGGT

GATTATGCATTTGACTTTGAAGAGGTTATCCGCAAAAATTCGTATGGCA

GAAACATTGATCAACTGGtacgttctttctgaaaagtactgctaaata tgatatactgtttctgtttatatagaaatgtttcgttggtgtaatacat catacatgtgagaaatgagatttcctagaatgattaccgcatccatatt tttctttactagcaccttttttttttgctttgtaagtgaaatgtggctg acattgactatgatatgacgagagtttgtactcttgggaaattgcgtta ggacttattgctttaaggttattatgatagatatgagacgttgcaacac ttcttatgaaatgcattgtccttctgtttctcattgactcttagctgtt ctttgtcactttcagCTGCTCTCACCCAACTAGGCGAAAAGACAACTCT TGTATCACCTGAGATGATAATTGCATCTGACATTCCCTGCTGTAGgtag gccttttaattttatttgaactttcacttctgttatgtggagatgtgag gcagtttgtgttttcttataactacgccaagctctgctatatctatttt tgttttcccacgtagGTTGGTACAGAATCCTGGTGAATTTGTTGTGACT TTTCCGAGGTCTTATCATGTAGGATTCAGCCACGgtaaaaatgcttttt ttcttcaaacattcttaagtctttgtgactttactttggtcgtcccatt ttgcactcttcaaagtgtgtgagaaaatgtgaaaattcaaaattcaaaa ttgagtaaagctttggagaaaaatgagtgttttacgacagagcataagg tgaggattgatcttctaattaggagaatgaagaaccaaatttctattaa gtagtagttatataagttgcatagtaaaagcggatagtttggcttcgat taggaatacaaattgcaatattttttcagaatccttaactaagcagaa ttaatttaacgttttaaagGTTTTAACTGTGGGGAAGCCGCTAATTTTG

GAACTCCACAATGGCTCAACGTAGCTAAGGAAGCTGCTGTGCGACGGGC

AGCCATGAATTATCTTCCCATGCTGTCCCATCAGCAGCTGCTATATCTC

TTGACCATGTCCTTTGTTTCAAGGCAAATTTCCATGGCCTCTTTgtaca tagaacccttttctgctggaacctgttaatcctcatattcttgtaaata ttaaaattttcagAGTGCCACGATCATTACTACCAGGTGGTCGTAGCTC

CCGACTGAGAGATCGTCAGAGAGAAGAAAGGGAGTTCCTTGTGAAAAAA

GCTTTTGTAGAAGATATACTGAACGAAAACAAGAATTTATCTGTTCTTC

ATCGAGAACCGGGATTTCGTTTGGTGATGTGGGACCCTGATTTACTCCC

GCGTCATAGTGTACATGGTCTTGTAACTGTTGGGGGTGCTGCTGTTTCA

TCTCCAGCAGAGGGAAAAAATGAACTTGAGGAGAAGAATAAAGAGAAGA

CTACTCTTTTAGAGGAATTGAGTTTGTTCATGGAGAAGCTGAAAGATGT
```

ATACTACGACGATGATGATGGTCTGCTTAATGATTTCCAGGTTGATTCT

GGAACCTTGGCATGTGTGGCGTGTGGCGTTCTTGGCTTCCCCTTTATGT

CTGTGGTACAGCCTTCTGAAAATGCATTAAATGATCTTTCAGAGAGACG

AGGAGAGATAGgtaacagaccctcattttttaaccaaactatgaacta caccatcttcgtttgaagcctgttaattgtgcttctatctattctacag

ATGGTCAGGAAATTACGGCACTGTTGTCAGAAAAGTCTGACTGTGAATG

GAACATGTCCTCCAGGTATATAAGACCTCGCATTTTCTGCCTCGAACAC

ACTATTGAGCTCCAGAGACTGCTGGAGTCACGAGGTGGACTGAAGTTCC

TTGTAATTTGCCATAAAGgtaagtacgcgtcatttgctattaaattcga tgccaaagagaatattttgatcattctgcttttaactttttttggaatt gttgcagACTTTCAAAAATTTAAGGCATATGCGGCTATAGTGGCAGAGG

AAGTTAAAGTCCCTTTCAGCTATGATGATATCCTGTTAGAGAGTGCATC

TAAAGAAGAGTTGAGTCTGATTGATCTTGCAATTGAAGATGAAGAAAAC

AACGAACATGGCGTAGACTGGACCTCAAAACTTGGTATCAATTTACGGT

ACTGTGTTAAAGTGAGGAAAAATTCCCCTTCTACGAAAATTCAGCATGC

ACTGTCGCTAGGTGGCTTGTTCTCCGATACAAACCACATGCTAGATATG

TCAACTATCAAATGGCTGCAGAGAAAATCACGCTAAAAGCCAAACCCA

GTTGTACCTCAAGCTTCACACCTCGTGAACATCTTGAAGTAAAAGTAGA

CAGAAAATTAGGGGAGAAGGAAAAAGTTGAATCCCAAGCCGGAAGAAAG

GAAGAAAAGATCATCCAGTACTCGAGAAAGAAAAAGTTGAAGCCCAAGC

CTTCTGAAGAACGAAGTCAGGAACTAACTATCTCAGCTAAATCAGAAGA

TTTTGAAAACATGCAACACACTTGCCAAAAGGTCACATCATCATGGG

GCAATGCATTCTGATATGAACAATGAAATTGGAGATTTTGGGAGGAATG

GGGTATCCTTTTCAGAAAATCATTGTAGCTCACCTTTCACTGGGGCACG

CGGACAAGAACATCCCAAGATCATTATCAAGTTTGGCTCAGCATTACAT

GGGAATATTACAAGCAGTTCTAGTTTGGTGAATGGAATCTCTGCTGACC

TAACTTCCGTAACCAGAGAGCACCAAGGACACTCTATGACCAGCAATAA

TAATGGGTCGAACTCAAGTAATCATGATGGCCCAATAAAGCTGTCTGGT

GAGCATGTCAGTGACGTGTCTGTACGTGATGTTGATGAAGCGGTTGAAA

TGAGCGACCAAGAGTTCGAAGAACTGAGGTCTACCGTCACTAACATTGA

GGAGGAACAGCAATCAGAGATGGTGAGACCAACCGCACTTCAGGTGGAG

GGAGAGGAATCTATGTGTACGAGAGAAATCTTGAGCTCTGAAGATATTA

TGCACACTGAGCAGCAGCAAGAGCAAACTCAACTGGGTTTAGAAGTTCC

TGAAACTGACATTGCCAGTGAGAACATAGTTGTGGACATGATCCATGAT

GATGAACCTCTGGCAACTAGGGATATATTAAGTTCAAGCAACGGTGATC

AAGCTTCTTCAAATGGCTTGCAAGCTCTAGATAATGAACTTAGCATGGA

GAGCGAAGTTGCAAGCTCAGAAAACACCGAGGTTATAGAGGCGTCGCCC

AATTCTATTATGCGAGAAGCAAATAAGAAGCGGAGAATAGAATCAGAGT

CTGAGACAAATGATAATCCAGATGGTAGCATTGGTTTCATAAGGAGTCC

TTGTGAAGGGTTGAGGTCAAGGGGTAGGAGGAGAGTGACGCGTGAAGCT

TCAGTCAGTCTCACTGAAACGAGCGATGAAGAGAAGAAACCCGCTGCGA

AAAGGTTCAAGAAAACTCCAAAGACTCGCTCGGGGAGTCATCACCAAGA

AGACTCCACGACAAGTCACCACAACCGTTGTAACCTAGAGGGATGCAAG

ATGACTTTCAAGAGTAAAGCAGAGTTACAAGCTCACCAAAGAAACCGCT

GCGCACATGAAGGGTGTGGAAAAAAATTCAGGGCTCACAAATATCTGGT

GCTTCATCAACGTGTTCATAACGATGATAGACCTTTTGTGTGCTCTTGG

AAAGGATGTTCCATGACTTTCAAATGGCCATGGGCGAGGACCGAGCATT

TGCGTCTGCACACGGGAGAGCGACCATACAAATGCAAGGTCGATGGATG

TGGAATGTCGTTTAGGTTTGTGTCGGATTACAGCCGCCATAGACGGAAA

AAGGGGCATTATGTGACATAG

A modified pennycress ELF6 coding sequence having a single base-pair substitution (e.g., SEQ ID NO:3) can result in ELF6 polypeptide having modified function (e.g., a modified ELF6 polypeptide having reduced ELF6 polypeptide expression and/or reduced ELF6 polypeptide function). For example, a modified pennycress ELF6 coding sequence having a single base-pair substitution (e.g., SEQ ID NO:3) can encode a modified ELF6 polypeptide. In some cases, a modified ELF6 polypeptide can include a substitution of the histidine (H) at amino acid residue 318 in a WT pennycress ELF6 protein (e.g., SEQ ID NO:2). The H at amino acid residue 318 can be substituted with any appropriate amino acid (e.g., tyrosine (Y)). For example, a modified ELF6 coding sequence can include a single Y substituted for the H at amino acid residue 318 in a WT pennycress ELF6 polypeptide (see, e.g., FIG. 4C). A representative modified pennycress ELF6 polypeptide is as follows (SEQ ID NO:4), with the bold, italic Y indicating the substitution.

MGDVEIPNWLKALPLAPVFRPTDTEFADPIAYISKIEKEASAFGICKII

PPLPKPSKKYVFYNLNKSLLRCPELASDVDISKVCQEDRAVFTTRQQEL

GQAVKRKKGGESSKSNSQRSGVKQVWQSGGVYTLEQFESKSKTFYKSQL

GTTKEVPPVVVEALFWKAALEKPIYIEYANDVPGSAFGEPEGHFRHFRQ

RKRRGRGFYQRKAEVSEDSGVENGTNSQEPTCKNGEKTLPEVAKASLAS

PSLLSQDPSKQKNMDIVDEMEGTAGWKLSNSSWNLQMIARSPGSVTRFM

PDDIPGVTSPMVYIGMLFSWFAW*Y*VEDHELHSMNYLHIGSPKTWYAVPG

DYAFDFEEVIRKNSYGRNIDQLAALTQLGEKTTLVSPEMIIASDIPCCR

LVQNPGEFVVTFPRSYHVGFSHGFNCGEAANFGTPQWLNVAKEAAVRRA

AMNYLPMLSHQQLLYLLTMSFVSRQISMASLVPRSLLPGGRSSRLRDRQ

REEREFLVKKAFVEDILNENKNLSVLHREPGFRLVMWDPDLLPRHSVHG

LVTVGGAAVSSPAEGKNELEEKNKEKTTLLEELSLFMEKLKDVYYDDDD

GLLNDFQVDSGTLACVACGVLGFPFMSVVQPSENALNDLSERRGEIDGQ

EITALLSEKSDCEWNMSSRYIRPRIFCLEHTIELQRLLESRGGLKFLVI

CHKDFQKFKAYAAIVAEEVKVPFSYDDILLESASKEELSLIDLAIEDEE

NNEHGVDWTSKLGINLRYCVKVRKNSPSTKIQHALSLGGLFSDTNHMLD

MSTIKWLQRKSRSKAKPSCTSSFTPREHLEVKVDRKLGEKEKVESQAGR

KEEKIIQYSRKKKLKPKPSEERSQELTISAKSEDFENTCNTLAKRSHHH

-continued

```
GAMHSDMNNEIGDFGRNGVSFSENHCSSPFTGARGQEHPKIIIKFGSAL

HGNITSSSSLVNGISADLTSVTRSNHDGPIKLSGEHVSDVSVRDVDEAV

EMSDQEFEELRSTVTNIEEEQQSEMVRPTALQVEGEESMCTREILSSED

IMHTEQQQEQTQLGLEVPETDIASENIVVDMIHDDEPLATRDILSSSNG

DQASSNGLQALDNELSMESEVASSENTEVIEASPNSIMREANKKRRIES

ESETNDNPDGSIGFIRSPCEGLRSRGRRRVTREASVSLTETSDEEKKPA

AKRFKKTPKTRSGSHHQEDSTTSHHNRCNLEGCKMTFKSKAELQAHQRN

RCAHEGCGKKFRAHKYLVLHQRVHNDDRPFVCSWKGCSMTFKWPWARTE

HLRLHTGERPYKCKVDGCGMSFRFVSDYSRHRRKKGHYVT
```

In some cases, the early flowering oilseed plants described herein can be from the A7 25 as described, for example, in Example 1, or can be progeny derived from that line.

In some cases, an early flowering oilseed plants described herein also can include increased oil quality. As used herein, an oilseed plant having "increased oil quality" can have an altered fatty acid profile such that the oil produced by the plant is suitable for human consumption. In some cases, oilseed plants provided herein having an altered fatty acid profile can have a "low level" or an "elevated level" of a particular fatty acid as compared to a reference level of the same fatty acid. The term "low level" as used herein with respect to a level of fatty acid in an oilseed plant refers to any level that is lower than (e.g., reduced or decreased) a reference level of the same fatty acid. The term "elevated level" as used herein with respect to a level of fatty acid in an oilseed plant refers to any level that is higher than (e.g., increased) a reference level of the same fatty acid. The term "reference level" as used herein with respect to a particular fatty acid refers to the level of the fatty acid typically observed in a wild type oilseed plant. It will be appreciated that levels of a particular fatty acid from comparable oilseed plants are used when determining whether or not the level of the fatty acid in a particular oilseed plant is a low level or an elevated level. In some cases, an oilseed plant having an altered fatty acid profile described herein also can have a low level of linoleic acid (18:02). For example, a low level of linoleic acid can be a level that is from about 0% to about 15% (by weight) linoleic acid (e.g., from about 0% to about 12%, from about 0% to about 10%, from about 0% to about 7%, from about 0% to about 5%, from about 3% to about 15%, from about 5% to about 15%, from about 8% to about 15%, from about 10% to about 15%, from about 12% to about 15%, from about 3% to about 14%, from about 5% to about 13%, or from about 7% to about 12% (by weight) linoleic acid). For example, a low level of linoleic acid can be a level that is about 10% (by weight) linoleic acid. In some cases, an oilseed plant having an altered fatty acid profile described herein also can have an elevated level of oleic acid (18:01). For example, an elevated level of oleic acid can be a level that is from about 20% to about 35% (by weight) oleic acid (e.g., from about 20% to about 32%, from about 20% to about 30%, from about 20% to about 27%, from about 20% to about 25%, from about 23% to about 35%, from about 25% to about 35%, from about 28% to about 35%, from about 30% to about 35%, from about 22% to about 35%, from about 23% to about 34%, from about 25% to about 33%, or from about 27% to about 32% (by weight) oleic acid). For example, an elevated level of oleic acid can be a level that is about 30% (by weight) oleic acid.

Figure 6A:
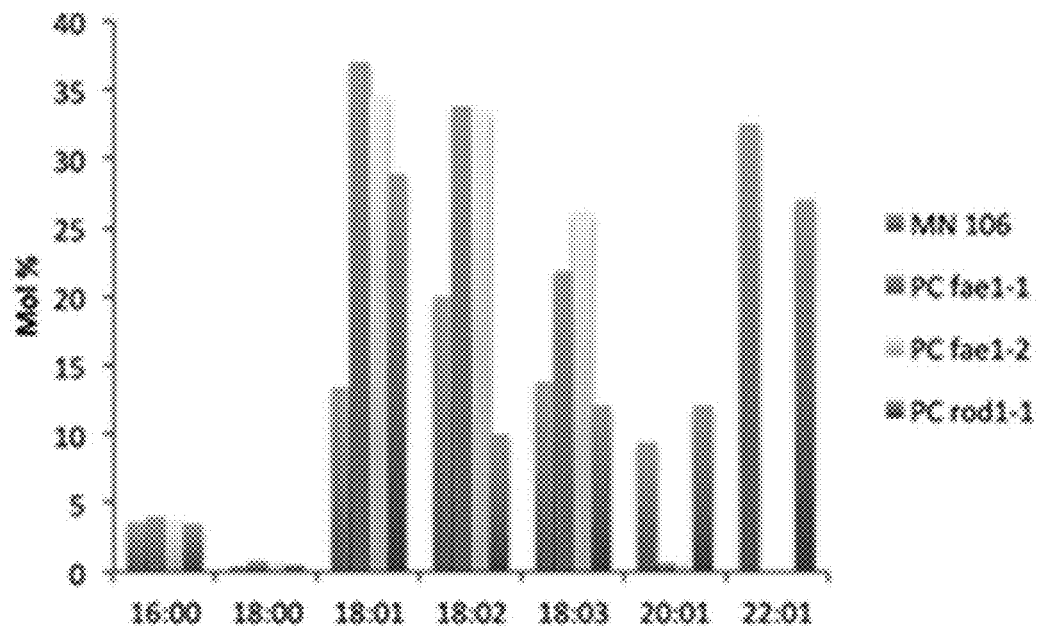

In some cases, oilseed plants having an altered fatty acid profiles as described herein can have a low level of linoleic acid and an elevated level of oleic acid (see, e.g., FIG. 6A). Oilseed plants having an altered fatty acid profile as described herein can be identified by, for example, an NIR analyzer (e.g., as described in the Examples).

In some cases, early flowering oilseed plants provided herein having one or more modifications in a polypeptide involved in early flowering (e.g., ELF6) also can include one or more modifications in a gene that encodes a polypeptide involved in fatty acid biosynthesis. Polypeptides involved in fatty acid biosynthesis include, without limitation, reduced oleate desaturation 1 (ROD1), fatty acid elongase 1 (FAE1), and fatty acid desaturates 2 (FAD2). In some cases, an early flowering oilseed plants described herein also can include reduced expression levels of ROD1, as compared to corresponding wild type plants. A representative WT pennycress ROD1 gene (e.g., coding sequence) is as follows (SEQ ID NO:5), with lower case letters indicating introns.

```
ATGTCAACTAAAACCGTCGTCCCTCTCCGTCGCAGATCTAAGCCCCTTA

ACGGAAATCACACTAACGGCGTCGCCATTGACGGAAGCCTCGACGACGA

CCACAACCGTCGCATCGGATCAGTAAATAGCCAAATGGATAACATTGCT

AAGAAAACGGACGACGGCTACGCAAACGGCGGAGGAGGAGGAGGAGGAG

GGAAAAGCAAGGCGTCGTTTATGACGTGGACGGCGCGTGACGTTGTGTA

CGTGGCGAGGTACCATTGGATACCGTGTTTGTTCGCGGTCGGGGTTCTG

TTCTTCACGGGCGTGGAGTACACGCTCCAGATGATTCCCGCGAGGTCTG

AGCCGTTCGATATTGGGTTTGTGGCCACGCGCTCTCTGAATCGCGTCTT

GGCAAATTCACCGGATCTTAACACCGTCTTAGCCGCTCTAAACACGgta atttcgtactaattaatttagggtaaaaaatatagtatttaataatgac tatcctcaattcctttcatgcttcacctaatattttgtttttttcgtt gtcattaaaatcgtaataatatattgagttagtcaaatgaaaaaaacaa gtggcggtagtgattggaaacaaatctcagatcttttatctgtttaata aggtatttaattatccagctggaattatgctgtcaagtgtcaacacagt agtagtaacatgcaatggaatttctcaatagaaaaaggtcttaattagt atagataattagtggacaaaaatgtagttaatgtaatctctttgctaag tagttatcataatcatcttttaacaactgccattttgtctgtgtgttt gttttacaacgaagtagtagtagaatagatcgcttttagcttttgaaa gtttcgaacccaaggaaaagggacacatgggttatgagttggagacacg atcacatgcaaacagagagattggttaaattatcgacttttgtagtac tttttaaaaaaaaactatttatataaaaaacatggtggatggtggggac agGTGTTCGTAGGGATGCAAACGACGTATATTGTATGGACATGGTTAAT

GGAAGGACGACCACGAGCCACCATCTCGGCTTGCTTCATGTTTACTTGT

CGAGGCATTCTTGGTTACTCTACTCAGCTCCCTCTTCCTCAGgttccaa tcaacactttctttctatctcttttcttaattaaaataattaccaatta actaaatgctaatcagtcgatatatcatagttccaacgttttggacgtg tgatttccattggccactaccatataaaacaacagagtctctttattca ttattcaatatatatttgagtattgatattattcatagggaggtttcat
```

-continued
ttgtactatcaataaaatttctacaactcttggattttttctgctacat tttgtagttatttttttaattacttttaaaaacttgtgaataggagaga ctaatagtagtacgtaatatgattgtatcaaatgctttaacatgtgggg tttgggttaactatcatcatttcatagatcactattttgttttcgtttg ttacctaacttttttgttatctttgaaaaataatgttccacgagttgatt gactggacataaaaatcagattctctcactcatttacgttctacggttc tagccactcgttttttttcttttctttctgtggtgtaacacgtagataa tggattttctatgtgtgtcgtcttgctcaagaataataaatgtggttaa aggttaaatatagctctggaaattaattatctcctcttttttattaac cagGATTTTCTAGGATCAGGTGTCGATTTTCCGGTGGGAAACGTCTCGT

TCTTCCTCTTCTACTCGGGTCACGTCGCCGGTTCGATGATCGCATCTTT

GGACATGAGGAGAATGCAGAGGATGAGACTAGCGATGCTTTTTGACATC

CTCAATGTATTACAATCGATCAGGCTGCTCGGGACGAGAGGACACTACA

CGATTGATCTCGCTGTCGGAGTTGGCGCTGGGATTCTCTTTGATTCATT

CGCCGGCAAGTACGAAGAGATGATAAGCAAGAGACACAATTTAGTCAAT

GGTTTTGGTTTGATTTCGAAAGACTCGCTAGTCAATTAA

In some cases, a WT pennycress ROD1 *gene* (e.g., coding sequence) can have a sequence that deviates from the coding sequence set forth above (e.g., SEQ ID NO:5), sometimes referred to as a variant sequence, provided the variant sequence encodes a WT pennycress ROD1 polypeptide. A representative WT pennycress ROD1 polypeptide is as follows (SEQ ID NO:6).

MSTKTVVPLRRRSKPLNGNHTNGVAIDGSLDDDHNRRIGSVNSQMDNIA

KKTDDGYANGGGGGGGGKSKASFMTWTARDVVYVARYHWIPCLFAVGVL

FFTGVEYTLQMIPARSEPFDIGFVATRSLNRVLANSPDLNTVLAALNTV

FVGMQTTYIVWTWLMEGRPRATISACFMFTCRGILGYSTQLPLPQDFLG

SGVDFPVGNVSFFLFYSGHVAGSMIASLDMRRMQRMRLAMLFDILNVLQ

SIRLLGTRGHYTIDLAVGVGAGILFDSFAGKYEEMISKRHNLVNGFGLI

SKDSLVN

In some cases, a WT pennycress ROD1 polypeptide can have a sequence that deviates from the polypeptide sequence set forth above (SEQ ID NO:6), sometimes referred to as a variant sequence, provided the polypeptide maintains its WT function. For example, a ROD1 polypeptide can have at least 80 (e.g., at least 85, at least 90, at least 95, at least 98, or at least 99) percent sequence identity to SEQ ID NO:6. A ROD1 polypeptide can have one or more (e.g., 2, 3, 4, 5, 6, 7, 8, 9, or 10) amino acid modifications (e.g., substitutions) relative to SEQ ID NO:6.

In some cases, oilseed plants having an altered fatty acid profiles as described herein (e.g., a low level of linoleic acid and/or an elevated level of oleic acid) can include a loss-of-function modification in a rod1 gene (e.g., a rod1 coding sequence). For example, oilseed plants having a low level of linoleic acid and/or an elevated level of oleic acid can include a loss-of-function modification in a rod1 gene (e.g., a rod1 coding sequence). As used herein, a loss-of-function modification in a rod1 gene can be any modification that is effective to reduce ROD1 polypeptide expression or ROD1 polypeptide function. In some cases, reduced ROD1 polypeptide expression or reduced ROD1 polypeptide function can be eliminated ROD1 polypeptide expression or eliminated ROD1 polypeptide function. Examples of genetic modifications include, without limitation, deletions, insertions, substitutions, translocations, inversions, and duplications.

Figure 6B:
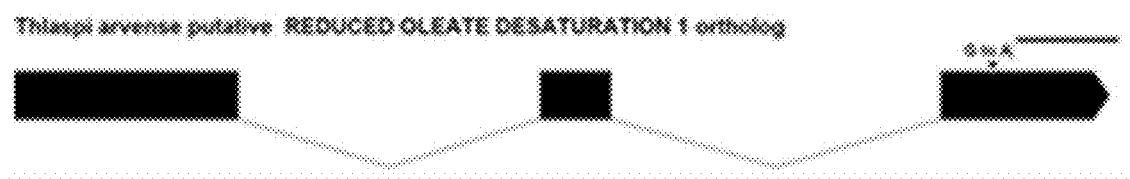

In some cases, oilseed plants having a low level of linoleic acid and/or an elevated level of oleic acid as described herein can include a substitution (e.g., a single base-pair substitution) relative to the WT pennycress rod1 coding sequence (e.g., SEQ ID NO:5). In some cases, a modified ROD1 polypeptide can include a single base-pair substitution of the G at nucleotide residue 1918 in a WT pennycress SPT coding sequence (e.g., SEQ ID NO:1). The G at residue 1918 can be substituted with any appropriate nucleotide (e.g., thymine (T), adenine (A), and cytosine (C)). For example, a single base-pair substitution can be a G to A substitution at nucleotide residue 1918 in a WT pennycress ROD1 coding sequence (see, e.g., FIG. 6B). A representative modified pennycress rod1 coding sequence having a loss-of-function single base pair substitution is as follows (SEQ ID NO:7), with the bold, italic A indicating the substitution and the lower case letters indicating introns.

ATGTCAACTAAAACCGTCGTCCCTCTCCGTCGCAGATCTAAGCCCCTTA

ACGGAAATCACACTAACGGCGTCGCCATTGACGGAAGCCTCGACGACGA

CCACAACCGTCGCATCGGATCAGTAAATAGCCAAATGGATAACATTGCT

AAGAAAACGGACGACGGCTACGCAAACGGCGGAGGAGGAGGAGGAGGAG

GGAAAAGCAAGGCGTCGTTTATGACGTGGACGGCGCGTGACGTTGTGTA

CGTGGCGAGGTACCATTGGATACCGTGTTTGTTCGCGGTCGGGGTTCTG

TTCTTCACGGGCGTGGAGTACACGCTCCAGATGATTCCCGCGAGGTCTG

AGCCGTTCGATATTGGGTTTGTGGCCACGCGCTCTCTGAATCGCGTCTT

GGCAAATTCACCGGATCTTAACACCGTCTTAGCCGCTCTAAACACGgta atttcgtactaattaatttagggtaaaaaatatagtatttaataatgac tatcctcaattcctttcatgcttcacctaatattttgttttttttcgtt gtcattaaaatcgtaataatatattgagttagtcaaatgaaaaaaacaa gtggcggtagtgattggaaacaaatctcagatcttttatctgtttaata aggtatttaattatccagctggaattatgctgtcaagtgtcaacacagt agtagtaacatgcaatggaatttctcaatagaaaaaggtcttaattagt atagataattagtggacaaaaatgtagttaatgtaatctctttgctaag tagttatcataatcatctttttaacaactgccattttgtctgtgtgttt gttttacaacgaagtagtagtagaatagatcgcttttttagcttttgaaa gtttcgaacccaaggaaaagggacacatgggttatgagttggagacacg atcacatgcaaacagagagattggttaaattatcgacttttttgtagtac tttttaaaaaaaaactatttatataaaaaacatggtggatggtggggac agGTGTTCGTAGGGATGCAAACGACGTATATTGTATGGACATGGTTAAT

GGAAGGACGACCACGAGCCACCATCTCGGCTTGCTTCATGTTTACTTGT

CGAGGCATTCTTGGTTACTCTACTCAGCTCCCTCTTCCTCAGgttccaa tcaacactttcttctatctcttttcttaattaaaataattaccaatta

```
actaaatgctaatcagtcgatatatcatagttccaacgttttggacgtg tgatttccattggccactaccatataaaacaacagagtctctttattca ttattcaatatatatttgagtattgatattattcatagggaggtttcat ttgtactatcaataaaatttctacaactcttggattttttctgctacat tttgtagttattttttttaattacttttaaaaacttgtgaataggagaga ctaatagtagtacgtaatatgattgtatcaaatgctttaacatgtgggg tttgggttaactatcatcatttcatagatcactattttgttttcgtttg ttacctaacttttttgttatctttgaaaaataatgttccacgagttgatt gactggacataaaaatcagattctctcactcatttacgttctacggttc tagccactcgttttttttcttttttctttctgtggtgtaacacgtagataa tggattttctatgtgtgtcgtcttgctcaagaataataaatgtggttaa aggttaaatatagctctggaaattaattatctcctctttttttattaac cagGATTTTCTAGGATCAGGTGTCGATTTTCCGGTGGGAAACGTCTCGT

TCTTCCTCTTCTACTCGGGTCACGTCGCCGGTTCGATGATCGCATCTTT

GGACATAAGGAGAATGCAGAGGATGAGACTAGCGATGCTTTTTGACATC

CTCAATGTATTACAATCGATCAGGCTGCTCGGGACGAGAGGACACTACA

CGATTGATCTCGCTGTCGGAGTTGGCGCTGGGATTCTCTTTGATTCATT

CGCCGGCAAGTACGAAGAGATGATAAGCAAGAGACACAATTTAGTCAAT

GGTTTTGGTTTGATTTCGAAAGACTCGCTAGTCAATTAA
```

A modified pennycress ROD1 coding sequence having a loss-of-function single base pair substitution (e.g., SEQ ID NO:7) can encode a modified ROD1 polypeptide (e.g., a modified ROD1 polypeptide having reduced ROD1 polypeptide expression and/or reduced ROD1 polypeptide function). For example, a modified pennycress ROD1 coding sequence having a single base-pair substitution (e.g., SEQ ID NO:7) can encode a modified ROD1 polypeptide. In some cases, a modified ROD1 polypeptide can include a substitution of the methionine (M) at amino acid residue 226 in a WT pennycress ROD1 protein (e.g., SEQ ID NO:2). The M at amino acid residue 226 can be substituted with any appropriate amino acid (e.g., isoleucine (I)). For example, a modified ROD1 coding sequence can include a single I substituted for the M at amino acid residue 226 in a WT pennycress ROD1 polypeptide (see, e.g., FIG. 4C). A representative modified pennycress ROD1 polypeptide is as follows (SEQ ID NO:8), with the bold, italic I indicating the substitution.

```
MSTKTVVPLRRRSKPLNGNHTNGVAIDGSLDDDHNRRIGSVNSQMDNIA

KKTDDGYANGGGGGGGKSKASFMTWTARDVVYVARYHWIPCLFAVGVL

FFTGVEYTLQMIPARSEPFDIGFVATRSLNRVLANSPDLNTVLAALNTV

FVGMQTTYIVWTWLMEGRPRATISACFMFTCRGILGYSTQLPLPQDFLG

SGVDFPVGNVSFFLFYSGHVAGSMIASLDIRRMQRMRLAMLFDILNVLQ

SIRLLGTRGHYTIDLAVGVGAGILFDSFAGKYEEMISKRHNLVNGFGLI

SKDSLVN
```

Representative sequences of modified FAE1 genes and modified FAE1 polypeptides can be as described elsewhere (see, e.g., U.S. 62/451,467).

Any appropriate method can be used to introduce one or more modifications into a gene involved in early flowering (e.g., ELF6) to produce early flowering oilseed plants described herein. Examples of methods for modifying an ELF6 coding sequence include, without limitation, genome editing (e.g., genome editing with engineered nucleases (GEEN)) and introduction of a transgene (e.g., gene transfer). For example, genome editing can be used to produce early flowering oilseed plants. Genome editing can insert, replace, or remove DNA from a genome using one or more site-specific nucleases (SSN) and, in some cases, a repair template (RT). Nucleases can be targeted to a specific position in the genome, where their action can introduce a particular modification to the endogenous sequences. For example, a SSN can introduce a targeted double-strand break (DSB) in the genome, such that cellular DSB repair mechanisms incorporate a RT into the genome in a configuration that produces heritable genome edits (e.g., a modification in an ELF6 coding sequence) in the cell, in a plant regenerated from the cell, and in any progeny of the regenerated plant. Nucleases useful for genome editing include, without limitation, Cas nucleases, zinc finger nucleases (ZFNs), transcription activator-like effector (TALE) nucleases, and homing endonucleases (HE; also referred to as meganucleases).

The genome editing reagents described herein can be introduced into an oilseed plant by any appropriate method. In some cases, nucleic acids encoding the genome editing reagents can be introduced into a plant cell using *Agrobacterium* or *Ensifer* mediated transformation, particle bombardment, liposome delivery, nanoparticle delivery, electroporation, polyethylene glycol (PEG) transformation, or any other method suitable for introducing a nucleic acid into a plant cell. In some cases, the SSN or other expressed gene editing reagents can be delivered as RNAs or as proteins to a plant cell and the RT, if one is used, can be delivered as DNA.

The invention will be further described in the following examples, which do not limit the scope of the invention described in the claims.

EXAMPLES

Example 1: Creation of Early Flowering Pennycress by EMS Mutagenesis

Materials and Methods

Mutagenesis (EMS, FN, and Gamma Ray).

20,000 pennycress seeds were treated with a solution of 0.2% ethyl methanesulfonate (EMS; the M1 generation). Seeds were split into 4 50 ml screw cap tubes containing 35 ml of EMS solution and were rotated for 18 hours at approximately 30 rpm on a rotating platform. Seeds were extensively rinsed with distilled water and then dried on filter paper.

Growth of Plants

In mid-August the EMS treated seeds were sowed into two 15 by 30 ft plots in fields. Emerging M1 seedlings were watered twice weekly until the middle of October. During the following June, the next generation of seeds (called the M2 generation) were collected from individual pools, each containing 10 M1 plants. In all, 500 pools of seed derived from 5000 M1 plants were recovered. The following August, approximately 300 seeds from each pool was sowed into an individual 10 feet row. In all, 500 rows of EMS treated seeds were planted. During the spring, plants were screened, and approximately 60 early flowering plants were identified.

These were replanted in the late summer. The early flowering phenotypes were reassessed the following spring.

Genetic Analysis of Plants

Approximately 100 mg of plant tissue was collected from A7-25 and used for DNA isolation. The DNA was isolated using the Qiagen Plant DNA Easy isolation kit. Whole genome sequencing was performed using the Illumina HiSeq 2000 sequencer.

Results

Figure 2:
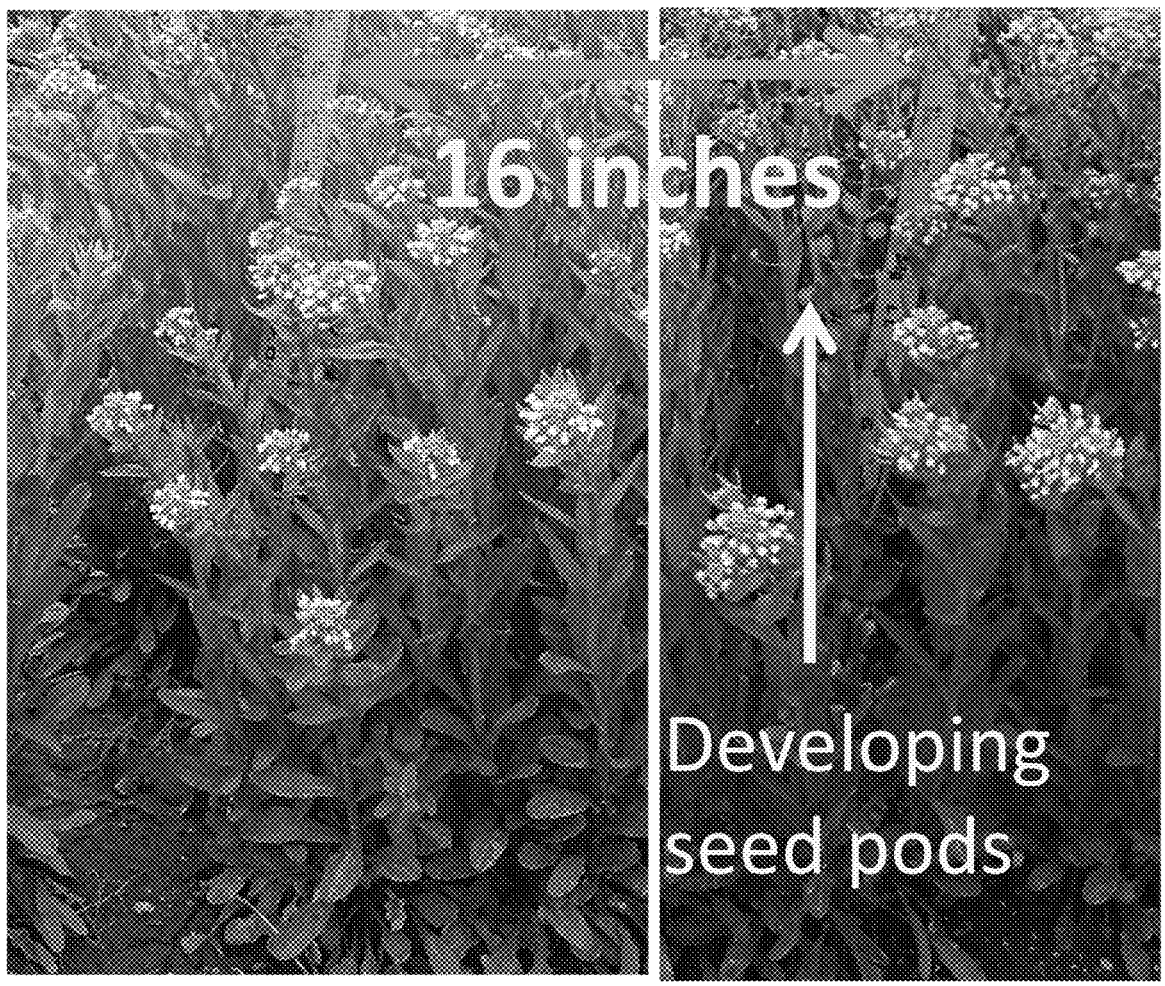
FIG. 2 contains images of pennycress plants in the field on April 25. On the left is a wild type (MN 106) pennycress plant. On the right is an A7 25 pennycress plant showing early seed pod development. Wild type control plants shown on the left did not developing pods until after May 6.
Figure 3:
FIG. 3 contains images of A7 25 pennycress plants in the field after experiencing a hard freeze overnight. A7 25 pennycress plants demonstrated little damage to young inflorescences, and recovered from any damage within 5 days.
Figures 5A, 5B:
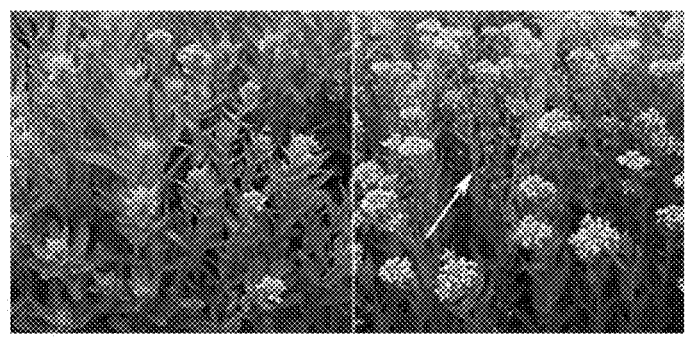
FIGS. 5A-5E contain images of early flowering pennycress plant. A and B) Wild type and early flowering pennycress grown in the field. The arrow in FIG. 5B highlights pod formation on the early flowering mutant that is absence on wild type. C and D) Wild type and early flowering pennycress grown in a growth room.
Figure 5C:
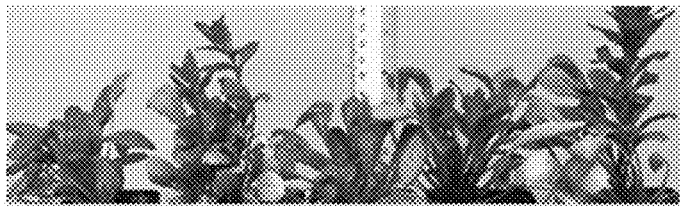
Figure 5D:
Figure 5E:
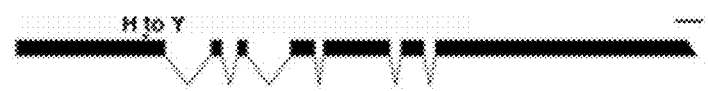

Approximately 20 lines showed early flowering compared to control plants. Line A7-25 showed the earliest flowering phenotype, flowering at least a week ahead of the others (FIG. 1), early seed pod development (FIG. 2), and recovery after a hard freeze (FIG. 3). The sequence reads were mapped to the wild type genome sequence. A C to T mutation was identified in the coding region of the pennycress ELF6 gene (FIG. 4).

These results demonstrate that an early flowering pennycress plant can be designed by modifying the ELF6 gene.

Example 2: Pennycress Plants Having Increased Oil Quality

Materials and Methods

Pennycress seeds were mutagenized and pennycress plants exhibiting domestication enabling traits such as increased oil quality were grown as described in Example 1.

NIR Spectral Analysis

M3 seeds were scanned using a Perten DA7250 NIR spectroscopy analyzer to assess the quality of oil seeds as described elsewhere (Sidhu et al., 2014 *Applied Engineering in Agriculture*, 30:69-76; Golebiowski et al, 2005 *Journal of near Infrared Spectroscopy*, 13:255-264; Riu et al., 2006 *Spectroscopy and Spectral Analysis*, 26:2190-2192; and Xin et al., 2014 *Journal of Agricultural and Food Chemistry*, 62:7977-7988).

Sequencing

PCR primers were designed to amplify the candidate pennycress genes (Table 1) and the products were subject to Sanger sequencing.

TABLE 1

PCR primers.

| primer | forward primer sequence | SEQ ID NO: | reverse primer sequence | SEQ ID NO: |
|---|---|---|---|---|
| ROD1 | GTGTGTCGTCTTGC TCAAGA | 9 | GTTCAAGTAATTAA CAGTATATTC | 10 |

Results

NIR spectral analyses captured information related to the approximate levels of the main fatty acids found in pennycress (eicosenoic, steric, palmitic, oleic, linoleic, linolenic, and erucic acids).

M4 seeds were collected from individual progeny during the following summer and subjected to NIR. The analysis identified a homozygous mutant containing low linoleic acid (FIG. 6A). This mutant was able to survive winter conditions. PCR and Sanger sequencing was use to analyze the candidate pennycress ROD1 ortholog (FIG. 6B) in the mutant, which revealed the presence of a substitution of isoleucine for a highly conserved methionine (FIG. 6C).

These results demonstrate that a pennycress plant with a low level of linoleic acid and an elevated level of oleic acid can be designed by modifying the ROD1 gene.

Example 3: Characterization of Early Flowering Pennycress

Materials and Methods

Pennycress seeds were mutagenized and pennycress plants exhibiting domestication enabling traits such as increased oil quality were grown as described in Example 1.

Measuring Days to Flower

F2 plants from a cross between the wild type GRIN accession Ames 23761 and the early flowering mutant MN A7-25 were planted into Ray Leach SC10 Cone-tainers™ filled with Sun Gro Metro Mix 560 Sun-Coir. After germination, plants were allowed to grow to the 2 true leaf stage in a 20° C. growth chamber. Plants were then transferred to a growth chamber maintained at 4° C. and 8 hours of light for a vernalization period of 21 days. After this period plants were returned to the 20° C. growth chamber. Days to flowering was recorded as the number of days after plants were returned to the 20° C. growth chamber to the first open florets visible on the plant.

DNA Extraction and SNP Genotyping

To perform co-segregation analysis on F2 and F3 families in elf6-1 populations, allele-specific and flanking primers were designed for each of the alleles (Table 2).

TABLE 2

Primers.

| primer | forward primer sequence | SEQ ID NO: |
|---|---|---|
| genotyping primers | | |
| elf6-1_common | ATCCCTGGTGTCAC ATCTCC | 16 |
| elf6-1_allele_specific_mut | GCTCATGGTCCTCA ACGTG | 17 |
| elf6-1_allele_specific_wt | TAAGCTCATGGTCC TCAACGTA | 18 |
| qPCR primers | | |
| ELF6-F-qpcr | CCTGGTGAATTTGT TGTGA | 19 |
| ELF6-R-qpcr | GGACAGCATGGGAA GATA | 20 |
| FLC-F-qpcr | GCTATCAACAAGCT TC | 21 |
| FLC-R-qpcr | GCACCATGAGCTAC TA | 22 |
| Actin-F-qpcr | GTGAGACACACCAT CACCAGAAT | 23 |
| Actin-R-qpcr | TGTCGCCATCCAAG CTGTTCT | 24 |
| Ubiquitin-F-qpcr | AGTTAAGAGGACTG TCTGG | 25 |
| Ubiquitin-R-qpcr | TCCTGAACCATATC CTCT | 26 |

Tails were used as described elsewhere (see, e.g., Rosas et al., 2014 *Electron. J. Biotechnol.* 17:95-101) to add to the 5' of the allele specific primers. DNA was extracted using Sigma ready extract method. Briefly, 1 cm² of tissue was sampled for each of the lines and dipped in the extraction buffer. Samples were incubated at 95° C. for 10 minutes followed by addition of dilution buffer. PCR mix consists of a final volume of 10 µl containing 1×KASP Reaction Mix (LGC Genomics, Hoddesdon, UK), 0.11 µl primer mix, and 1 µl of the DNA. End-point genotyping using Allele Specific chemistry was performed on a LightCycler 480 (Roche, Branford, Conn.) using parameters as described elsewhere (see, e.g., Chopra et al., 2015 BMC Genomics 16(1):1040).

RNA Extraction and Expression Analysis

For this study, leaf tissue from ten seedlings for each replicate were pooled for wild type (MN106) and mutant (A7-25) for RNA extractions. Three replicates for each line were extracted separately using the RNAeasy mini clean up kit (Qiagen, Valencia, Calif.) and treated with turbo DNase (ThermoFisher #AM2238). To evaluate the expression differences observed, qRT-PCR primers were designed for the pennycress ubiquitin and FLC genes. Briefly, qRT-PCR was performed using copy-DNA libraries generated from the total RNA using Invitrogen cDNA synthesis kit (Invitrogen, Grand Island, N.Y.). qRT-PCR was performed on the cDNA of the four samples with 3 biological and 3 technical replicates using SybrGreen on LightCycler 480. Expression of mutants and wild type were normalized using the references genes and we report the fold change in mutants compared to the wild type.

Results

Figure 7:
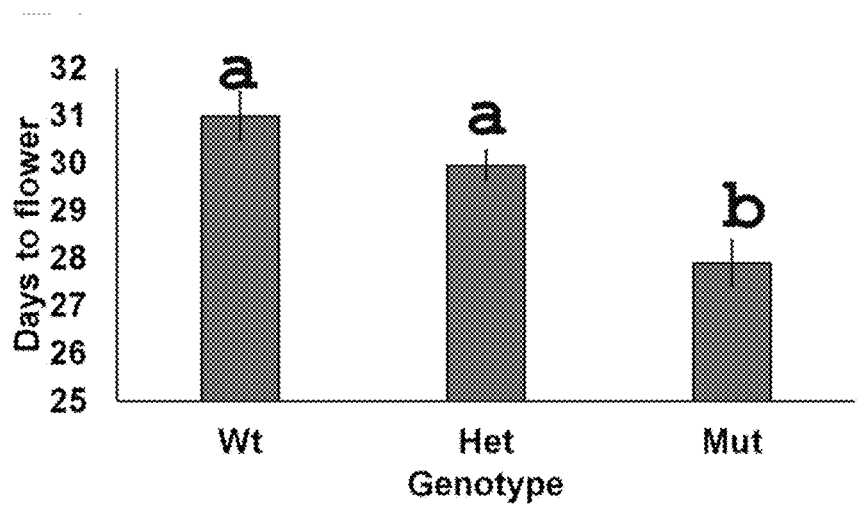
FIG. 7 contains a graph showing average days to flowering for an F2 population derived from a cross between wild type and the early flowering mutant. ELF6 KASP markers were used to assess the elf6-1 genotype of members in the F2 population.

To test for co-segregation between the ELF6 mutation and the early flowering phenotype, a cross was made between the mutant and the pennycress GRIN accession Ames 23761. KASP markers were used to genotype the F2 individuals (see Material and Methods). The average number of days to flower (±S.E.) for each plant of the F2 genotypic population is shown in FIG. 7. Only homozygous elf6 mutants showed early flowering. A one-way ANOVA analysis of the three datasets yielded a significant P-value of 0.00017 and a follow-up Tukey analysis yielded P-values indicating significant differences between the mutants and either homozygous wild type or heterozygous plants, 0.0002 and 0.0021, respectively. There was no significant difference between wild type and heterozygous plants for flowering time in this study.

Figure 8:
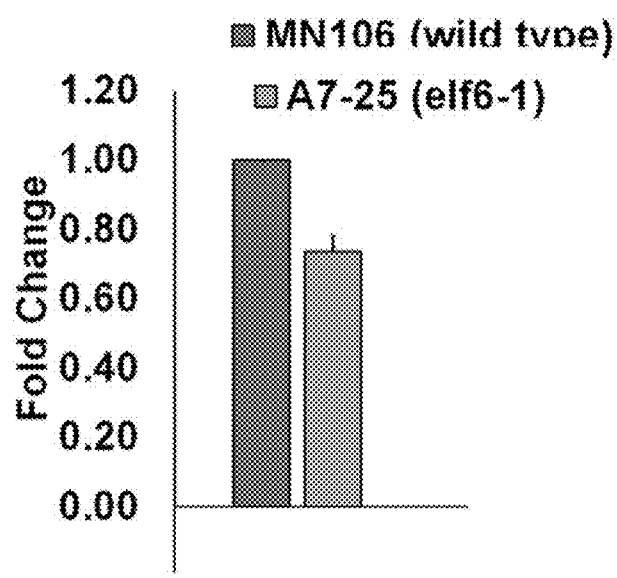
FIG. 8 contains a graph showing QPCR analysis of FLC expression in wild type and early flowering mutant plants using RNA from field grown plants collected in the fall of 2017. FLC gene expression values were normalized using an ubiquitin gene probe (error bar denotes standard deviation).

In Arabidopsis, ELF6 encodes a Histone 3-Lysine 27 (H3K27) demethylase that acts on the FLOWERING LOCUS C (FLC) locus (see, e.g., Crevillen et al., 2014 Nature 515(7528):587). FLC regulates the winter flowering habit and acts by preventing the expression of the flowering-inducing gene FLOWERING LOCUS T (FT) prior to vernalization. During vernalization, H3K27 associated with the FLC locus is methylated, which inactivates the expression of FLC and allows flowering. During Arabidopsis embryogenesis, FLC expression is reactivated in part by H3K27 demethylases, one of which is ELF6. This prevents early flowering, which is the key phenotype of Arabidopsis elf6 mutants. In Arabidopsis elf6 mutants, FLC expression is reduced in non-vernalized plants compared to wild type (see, e.g., Crevillén et al., 2014 Nature 515(7528):587). Thus, the levels of FLC expression were tested in fall planted field grown A7-25 compared to co-grown wild type. This study showed that, like Arabidopsis elf6 mutants, FLC expression was reduced by 67±8% (±S.D.) in the early flowering A7-25 line (FIG. 8). These findings strongly support the hypothesis that the ELF6 mutation in A7-25 is causative for the early flowering phenotype, hence we are designating this mutant allele Taelf6-1 or elf6-1.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An oilseed plant, wherein said oilseed plant flowers early as compared to a corresponding wild type oilseed plant, wherein said oilseed plant comprises an EARLY FLOWERING SIX (ELF 6) gene that encodes an ELF6 polypeptide having at least 95% sequence identity to the amino acid sequence set forth in SEQ ID NO:2 and having a substitution of the histidine (H) at amino acid residue 318 as numbered in SEQ ID NO: 2, wherein said ELF6 polypeptide has reduced polypeptide expression or reduced polypeptide function as compared to said wild type ELF6 polypeptide, and wherein said oilseed plant is selected from the group consisting of pennycress (*Tlaspi arvense* L.), rapeseed, soybean, sunflower, canola, flax, camelina, carinata, crambe, and lepidium plants.

2. The oilseed plant of claim 1, wherein said oilseed plant is a pennycress (*Thlaspi arvense* L.) plant.

3. The oilseed plant of claim 1, wherein said ELF6 gene comprises a substitution of the cytosine at residue 952, and wherein said substitution is a cytosine to thymine substitution.

4. The oilseed plant of claim 3, wherein said ELF6 gene comprises SEQ ID NO:3.

5. The oilseed plant of claim 1, wherein said ELF6 polypeptide comprises SEQ ID NO:4.

6. A seed produced by the oilseed plant of claim 1, wherein said seed comprises said gene.

* * * * *